(12) United States Patent
Gruendker et al.

(10) Patent No.: US 8,334,258 B2
(45) Date of Patent: Dec. 18, 2012

(54) METHOD FOR INDUCTION AND ENHANCEMENT OF APOPTOSIS IN TUMOR CELLS

(75) Inventors: Carsten Gruendker, Bovenden (DE); Andreas R. Guenthert, Goettingen (DE); Guenter Emons, Goettingen (DE)

(73) Assignee: Georg-August-Universität Göttingen Stiftung Öffentlichen Rechts (Universitätsmedizin), Goettingen (DE)

( * ) Notice: Subject to any disclaimer, the term of this patent is extended or adjusted under 35 U.S.C. 154(b) by 546 days.

(21) Appl. No.: 11/994,759

(22) PCT Filed: Jul. 20, 2006

(86) PCT No.: PCT/EP2006/007153
§ 371 (c)(1),
(2), (4) Date: Jan. 4, 2008

(87) PCT Pub. No.: WO2007/012430
PCT Pub. Date: Feb. 1, 2007

(65) Prior Publication Data
US 2008/0167250 A1    Jul. 10, 2008

(51) Int. Cl.
*A61K 38/08* (2006.01)
(52) U.S. Cl. .......... 514/15; 514/10.3; 514/10.1; 435/375
(58) Field of Classification Search .................. None
See application file for complete search history.

(56) References Cited

FOREIGN PATENT DOCUMENTS

| WO | WO 00/32218 | | 12/1999 |
|---|---|---|---|
| WO | WO 03/093304 | A1 | 3/2003 |
| WO | WO 01/74377 | A1 | 10/2003 |
| WO | WO 03/093304 | * | 11/2003 |

OTHER PUBLICATIONS

Emons et al., Endocrine Related Cancer, 2003, vol. 10, No. 2, pp. 291-299.*
Guenthert et al., Analogs of GnRH-I and GnRH-II inhibit epidermal growth factor-induced signal transductionand resensitize resistant human breast cancer cells to 4OH-tamoxifen, European Journal of Endocrinology/ European Federation of Endocrine Societies, Oct. 2005, vol. 153, No. 4, pp. 613-625.
Maiti et al: "Differential effects of gonadotropin-releasing hormone (GnRH)-I and GnRH-II on prostate cancer cell signaling and death", Journal of Clinical Endocrinology and Metabolism 2005 United States, vol. 90, No. &, pp. 4287-4298.
Carsten et al.: "Role of gonadotropin-releasing hormone (GnRH) in ovarian cancer", Reproductive Biology and Endocrinology [Electronic Resource]: RB&E. Oct. 7, 2003, vol. 1, pp. 1-7.
Emons et al.: "GnRH antagoists in the treatment of gynecological and breast cancers.", Endocrine-Related Cancer, Jun. 2003, vol. 10, No. 2, pp. 291-299 Wang et al.: Down-regulation of proliferation and up-regulation of apoptosis by gonadotropin-releasing hormone agonist in cultured uterrine leiomyoma cells, European Journal of Endocrinology, V.146,N3,Mar. 2002,.

* cited by examiner

*Primary Examiner* — Christopher R. Tate
*Assistant Examiner* — Roy Teller
(74) *Attorney, Agent, or Firm* — Whitham Curtis Christofferson & Cook, PC

(57) ABSTRACT

The present invention relates to methods for inducing and enhancing apoptosis in pathogenic cells. In particular, the present invention relates to the use of GnRH II antagonists for inducing and enhancing apoptosis of specific types of tumor cells, i.e. breast cancer and malignant melanoma as well as gynaecological cancers like endometrial or ovarian cancer, expressing the GnRH II receptor as well as to methods relating thereto. In addition, new GnRH II antagonists are provided.

4 Claims, 11 Drawing Sheets

SEQUENCE LISTING

```
<160> NUMBER OF SEQ ID NOS: 46

<210> SEQ ID NO 1
<211> LENGTH: 10
<212> TYPE: PRT
<213> ORGANISM: artificial sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X can represent Ac-D-2Nal, Ac-2Nal, Ac-D3Pro
<220> FEATURE:
<221> NAME/KEY: MISC_FEATURE
<222> LOCATION: (2)..(2)
<223> OTHER INFORMATION: X can represent His, D-4Cpa, Arg, Tyr, Trp,
      D-4Fpa, D-4Bpa
<220> FEATURE:
<221> NAME/KEY: MISC_FEATURE
<222> LOCATION: (3)..(3)
<223> OTHER INFORMATION: X can represent Trp, D-3Pal, D-2Nal, Ala, Phe,
      His,
<220> FEATURE:
<221> NAME/KEY: MISC_FEATURE
<222> LOCATION: (5)..(5)
<223> OTHER INFORMATION: X can represent Tyr, His
<220> FEATURE:
<221> NAME/KEY: MISC_FEATURE
<222> LOCATION: (6)..(6)
<223> OTHER INFORMATION: X can represent Gly, D-Lys, D-Cit, D-Trp,
      D-3Pal, D-2Nal
<220> FEATURE:
<221> NAME/KEY: MISC_FEATURE
<222> LOCATION: (7)..(7)
<223> OTHER INFORMATION: X can represent Trp, Leu, Arg
<220> FEATURE:
<221> NAME/KEY: MISC_FEATURE
<222> LOCATION: (8)..(8)
<223> OTHER INFORMATION: X can represent Tyr, Leu, Arg
<220> FEATURE:
<221> NAME/KEY: MISC_FEATURE
<222> LOCATION: (10)..(10)
<223> OTHER INFORMATION: X can represent Gly, Ala, D-Ala, D-Gly, D-Cys,
```

-continued

D-Ser, D-Val, D-Thr, D-Pro, D-Ile, D-Leu

<400> SEQUENCE: 1

Xaa Xaa Xaa Ser Xaa Xaa Xaa Xaa Pro Xaa
1               5                   10

<210> SEQ ID NO 2
<211> LENGTH: 10
<212> TYPE: PRT
<213> ORGANISM: artificial sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2 Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-3-Pal
<220> FEATURE:
<221> NAME/KEY: MISC_FEATURE
<222> LOCATION: (10)..(10)
<223> OTHER INFORMATION: X represents D-Ala-NH2

<400> SEQUENCE: 2

Xaa Xaa Xaa Ser His Xaa Trp Tyr Pro Xaa
1               5                   10

<210> SEQ ID NO 3
<211> LENGTH: 10
<212> TYPE: PRT
<213> ORGANISM: artificial sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (1)..(1)
<223> OTHER INFORMATION: X represents Ac-delta3Pro
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-2Nal
<220> FEATURE:
<221> NAME/KEY: MISC_FEATURE
<222> LOCATION: (10)..(10)
<223> OTHER INFORMATION: X represents Ala-NH2

<400> SEQUENCE: 3

Xaa Xaa Xaa Ser His Xaa Trp Tyr Pro Xaa
1               5                   10

<210> SEQ ID NO 4
<211> LENGTH: 10

-continued

```
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-2Nal
<220> FEATURE:
<221> NAME/KEY: MISC_FEATURE
<222> LOCATION: (10)..(10)
<223> OTHER INFORMATION: X represents Gly-NH2

<400> SEQUENCE: 4

Xaa Xaa Xaa Ser His Xaa Trp Tyr Pro Xaa
1               5                   10

<210> SEQ ID NO 5
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Cit
<220> FEATURE:
<221> NAME/KEY: MISC_FEATURE
<222> LOCATION: (10)..(10)
<223> OTHER INFORMATION: X represents Gly-NH2

<400> SEQUENCE: 5

Xaa Xaa Xaa Ser His Xaa Trp Tyr Pro Xaa
1               5                   10

<210> SEQ ID NO 6
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
```

```
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Lys
<220> FEATURE:
<221> NAME/KEY: MISC_FEATURE
<222> LOCATION: (10)..(10)
<223> OTHER INFORMATION: X represents Gly-NH2

<400> SEQUENCE: 6

Xaa Xaa Xaa Ser His Xaa Trp Tyr Pro Xaa
1               5                   10

<210> SEQ ID NO 7
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Trp
<220> FEATURE:
<221> NAME/KEY: MISC_FEATURE
<222> LOCATION: (10)..(10)
<223> OTHER INFORMATION: X represents Gly-NH2

<400> SEQUENCE: 7

Xaa Xaa Xaa Ser His Xaa Trp Tyr Pro Xaa
1               5                   10

<210> SEQ ID NO 8
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2 Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Cit
<220> FEATURE:
<221> NAME/KEY: MISC_FEATURE
<222> LOCATION: (10)..(10)
<223> OTHER INFORMATION: X represents Ala-NH2

<400> SEQUENCE: 8

Xaa Xaa Xaa Ser Tyr Xaa Trp Tyr Pro Xaa
```

```
1               5                   10

<210> SEQ ID NO 9
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2 Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Cit
<220> FEATURE:
<221> NAME/KEY: MISC_FEATURE
<222> LOCATION: (10)..(10)
<223> OTHER INFORMATION: X represents Ala-NH2

<400> SEQUENCE: 9

Xaa Xaa Xaa Ser His Xaa Trp Tyr Pro Xaa
1               5                   10

<210> SEQ ID NO 10
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2 Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Cit
<220> FEATURE:
<221> NAME/KEY: MISC_FEATURE
<222> LOCATION: (10)..(10)
<223> OTHER INFORMATION: X represents Ala-NH2

<400> SEQUENCE: 10

Xaa Xaa Xaa Ser Tyr Xaa Trp Leu Pro Xaa
1               5                   10

<210> SEQ ID NO 11
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2 Nal
<220> FEATURE:
```

```
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (6)..(6)
<223> OTHER INFORMATION: X represents D-Lys
<220> FEATURE:
<221> NAME/KEY: MISC_FEATURE
<222> LOCATION: (10)..(10)
<223> OTHER INFORMATION: X represents Gly-NH2

<400> SEQUENCE: 11

Xaa Xaa Ala Ser His Xaa Trp Tyr Pro Xaa
 1               5                  10

<210> SEQ ID NO 12
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2 Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (6)..(6)
<223> OTHER INFORMATION: X represents D-3-Pal
<220> FEATURE:
<221> NAME/KEY: MISC_FEATURE
<222> LOCATION: (10)..(10)
<223> OTHER INFORMATION: X represents Gly-NH2

<400> SEQUENCE: 12

Xaa Xaa Phe Ser His Xaa Trp Tyr Pro Xaa
 1               5                  10

<210> SEQ ID NO 13
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2 Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (6)..(6)
<223> OTHER INFORMATION: X represents D-3-Pal
<220> FEATURE:
<221> NAME/KEY: MISC_FEATURE
<222> LOCATION: (10)..(10)
<223> OTHER INFORMATION: X represents Gly-NH2

<400> SEQUENCE: 13

Xaa Xaa His Ser His Xaa Trp Tyr Pro Xaa
 1               5                  10

<210> SEQ ID NO 14
<211> LENGTH: 10
<212> TYPE: PRT
<213> ORGANISM: artificial Sequence
```

```
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2 Nal
<220> FEATURE:
<221> NAME/KEY: MISC_FEATURE
<222> LOCATION: (2)..(2)
<223> OTHER INFORMATION: X represents (4Cl)-D- Phe
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Lys
<220> FEATURE:
<221> NAME/KEY: MISC_FEATURE
<222> LOCATION: (10)..(10)
<223> OTHER INFORMATION: X represents Gly-NH2

<400> SEQUENCE: 14

Xaa Xaa Xaa Ser His Xaa Trp Tyr Pro Xaa
1               5                   10

<210> SEQ ID NO 15
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2 Nal
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Lys
<220> FEATURE:
<221> NAME/KEY: MISC_FEATURE
<222> LOCATION: (10)..(10)
<223> OTHER INFORMATION: X represents Gly-NH2

<400> SEQUENCE: 15

Xaa Arg Xaa Ser His Xaa Trp Tyr Pro Xaa
1               5                   10

<210> SEQ ID NO 16
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2 Nal
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-3-Pal
<220> FEATURE:
<221> NAME/KEY: MISC_FEATURE
<222> LOCATION: (10)..(10)
<223> OTHER INFORMATION: X represents Gly-NH2
```

```
<400> SEQUENCE: 16

Xaa Tyr Xaa Ser His Xaa Trp Tyr Pro Xaa
1               5                   10

<210> SEQ ID NO 17
<211> LENGTH: 10
<212> TYPE: PRT
<213> ORGANISM: artificial Sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2 Nal
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Lys
<220> FEATURE:
<221> NAME/KEY: MISC_FEATURE
<222> LOCATION: (10)..(10)
<223> OTHER INFORMATION: X represents Gly-NH2

<400> SEQUENCE: 17

Xaa Trp Xaa Ser His Xaa Trp Tyr Pro Xaa
1               5                   10

<210> SEQ ID NO 18
<211> LENGTH: 10
<212> TYPE: PRT
<213> ORGANISM: homo sapiens
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (10)..(10)
<223> OTHER INFORMATION: Gly-NH2

<400> SEQUENCE: 18

Glu His Trp Ser His Gly Trp Tyr Pro Gly
1               5                   10

<210> SEQ ID NO 19
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (5)..(5)
<223> OTHER INFORMATION: X represents N-Met-Tyr
<220> FEATURE:
<221> NAME/KEY: MISC_FEATURE
<222> LOCATION: (6)..(6)
```

```
<223> OTHER INFORMATION: X represents D-Asn
<220> FEATURE:
<221> NAME/KEY: MISC_FEATURE
<222> LOCATION: (8)..(8)
<223> OTHER INFORMATION: X represents Ilys
<220> FEATURE:
<221> NAME/KEY: MISC_FEATURE
<222> LOCATION: (10)..(10)
<223> OTHER INFORMATION: X represents D-Ala-NH2

<400> SEQUENCE: 19

Xaa Xaa Xaa Ser Xaa Xaa Leu Xaa Pro Xaa
1               5                   10

<210> SEQ ID NO 20
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (5)..(5)
<223> OTHER INFORMATION: X represents Aph (Ac)
<220> FEATURE:
<221> NAME/KEY: MISC_FEATURE
<222> LOCATION: (6)..(6)
<223> OTHER INFORMATION: X represents D-Aph (Ac)
<220> FEATURE:
<221> NAME/KEY: MISC_FEATURE
<222> LOCATION: (8)..(8)
<223> OTHER INFORMATION: X represents Ilys
<220> FEATURE:
<221> NAME/KEY: MISC_FEATURE
<222> LOCATION: (10)..(10)
<223> OTHER INFORMATION: X represents D-Ala-NH2

<400> SEQUENCE: 20

Xaa Xaa Xaa Ser Xaa Xaa Leu Xaa Pro Xaa
1               5                   10

<210> SEQ ID NO 21
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-(Hci)
<220> FEATURE:
```

```
<221> NAME/KEY: MISC_FEATURE
<222> LOCATION: (8)..(8)
<223> OTHER INFORMATION: X represents Ilys
<220> FEATURE:
<221> NAME/KEY: MISC_FEATURE
<222> LOCATION: (10)..(10)
<223> OTHER INFORMATION: X represents D-Ala-NH2

<400> SEQUENCE: 21

Xaa Xaa Xaa Ser Tyr Xaa Leu Xaa Pro Xaa
1               5                   10

<210> SEQ ID NO 22
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (5)..(5)
<223> OTHER INFORMATION: X represents Lys (Nic)
<220> FEATURE:
<221> NAME/KEY: MISC_FEATURE
<222> LOCATION: (6)..(6)
<223> OTHER INFORMATION: X represents D-Asn
<220> FEATURE:
<221> NAME/KEY: MISC_FEATURE
<222> LOCATION: (8)..(8)
<223> OTHER INFORMATION: X represents Ilys
<220> FEATURE:
<221> NAME/KEY: MISC_FEATURE
<222> LOCATION: (10)..(10)
<223> OTHER INFORMATION: X represents D-Ala-NH2

<400> SEQUENCE: 22

Xaa Xaa Xaa Ser Xaa Xaa Leu Xaa Pro Xaa
1               5                   10

<210> SEQ ID NO 23
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (5)..(5)
<223> OTHER INFORMATION: X represents Lys (Atz), [5'-(3'-amino-1H-1',
      2',4'-triazoyl)]
<220> FEATURE:
<221> NAME/KEY: MISC_FEATURE
```

```
<222> LOCATION: (6)..(6)
<223> OTHER INFORMATION: X represents D-Lys (Atz), [5'-(3'-amino-1H-1',
      2',4'-triazoyl)]
<220> FEATURE:
<221> NAME/KEY: MISC_FEATURE
<222> LOCATION: (8)..(8)
<223> OTHER INFORMATION: X represents Ilys
<220> FEATURE:
<221> NAME/KEY: MISC_FEATURE
<222> LOCATION: (10)..(10)
<223> OTHER INFORMATION: X represents D-Ala-NH2

<400> SEQUENCE: 23

Xaa Xaa Xaa Ser Xaa Xaa Leu Xaa Pro Xaa
1               5                   10

<210> SEQ ID NO 24
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (5)..(5)
<223> OTHER INFORMATION: X represents Aph (Atz), [5'-(3'-amino-1H-1',
      2',4'-triazoyl)]
<220> FEATURE:
<221> NAME/KEY: MISC_FEATURE
<222> LOCATION: (6)..(6)
<223> OTHER INFORMATION: X represents D-Aph (Atz), [5'-(3'-amino-1H-1',
      2',4'-triazoyl)]
<220> FEATURE:
<221> NAME/KEY: MISC_FEATURE
<222> LOCATION: (8)..(8)
<223> OTHER INFORMATION: X represents Ilys
<220> FEATURE:
<221> NAME/KEY: MISC_FEATURE
<222> LOCATION: (10)..(10)
<223> OTHER INFORMATION: X represents D-Ala-NH2

<400> SEQUENCE: 24

Xaa Xaa Xaa Ser Xaa Xaa Leu Xaa Pro Xaa
1               5                   10

<210> SEQ ID NO 25
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
```

```
<221> NAME/KEY: MISC_FEATURE
<222> LOCATION: (6)..(6)
<223> OTHER INFORMATION: X represents D-Cit
<220> FEATURE:
<221> NAME/KEY: MISC_FEATURE
<222> LOCATION: (10)..(10)
<223> OTHER INFORMATION: X represents D-Ala-NH2

<400> SEQUENCE: 25

Xaa Xaa Xaa Ser Tyr Xaa Leu Arg Pro Xaa
1               5                   10

<210> SEQ ID NO 26
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (5)..(5)
<223> OTHER INFORMATION: X represents Aph (L-Hor), Hor is hydroorotyl;
<220> FEATURE:
<221> NAME/KEY: MISC_FEATURE
<222> LOCATION: (6)..(6)
<223> OTHER INFORMATION: X represents D-Aph (Cbm), Cbm is carbamoyl;
<220> FEATURE:
<221> NAME/KEY: MISC_FEATURE
<222> LOCATION: (8)..(8)
<223> OTHER INFORMATION: X represents Ilys
<220> FEATURE:
<221> NAME/KEY: MISC_FEATURE
<222> LOCATION: (10)..(10)
<223> OTHER INFORMATION: X represents D-Ala-NH2

<400> SEQUENCE: 26

Xaa Xaa Xaa Ser Xaa Xaa Leu Xaa Pro Xaa
1               5                   10

<210> SEQ ID NO 27
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents hArg(Et)2
<220> FEATURE:
<221> NAME/KEY: MISC_FEATURE
<222> LOCATION: (8)..(8)
```

```
<223> OTHER INFORMATION: X represents hArg(Et)2
<220> FEATURE:
<221> NAME/KEY: MISC_FEATURE
<222> LOCATION: (10)..(10)
<223> OTHER INFORMATION: X represents D-Ala-NH2

<400> SEQUENCE: 27

Xaa Xaa Xaa Ser Tyr Xaa Leu Xaa Pro Xaa
1               5                   10

<210> SEQ ID NO 28
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents 5-oxo-Pro
<220> FEATURE:
<221> NAME/KEY: MISC_FEATURE
<222> LOCATION: (6)..(6)
<223> OTHER INFORMATION: X represents D-2Nal
<220> FEATURE:
<221> NAME/KEY: MISC_FEATURE
<222> LOCATION: (10)..(10)
<223> OTHER INFORMATION: X represents D-Ala-NH2

<400> SEQUENCE: 28

Xaa His Trp Ser Tyr Xaa Leu Arg Pro Xaa
1               5                   10

<210> SEQ ID NO 29
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents p-mb-D-2Abu, (p-methoxybenzoyl)-
      D-2Abu;
<220> FEATURE:
<221> NAME/KEY: MISC_FEATURE
<222> LOCATION: (10)..(10)
<223> OTHER INFORMATION: X represents D-Ala-NH2

<400> SEQUENCE: 29

Xaa Xaa Xaa Ser Arg Xaa Leu Arg Pro Xaa
1               5                   10

<210> SEQ ID NO 30
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
```

```
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (5)..(5)
<223> OTHER INFORMATION: X represents PicLys, N-picolinoyllysine
<220> FEATURE:
<221> NAME/KEY: MISC_FEATURE
<222> LOCATION: (6)..(6)
<223> OTHER INFORMATION: X represents D-(6-amino-Nic)-Orn
<220> FEATURE:
<221> NAME/KEY: MISC_FEATURE
<222> LOCATION: (8)..(8)
<223> OTHER INFORMATION: X represents Ilys
<220> FEATURE:
<221> NAME/KEY: MISC_FEATURE
<222> LOCATION: (10)..(10)
<223> OTHER INFORMATION: X represents D-Ala-NH2

<400> SEQUENCE: 30

Xaa Xaa Xaa Ser Xaa Xaa Leu Xaa Pro Xaa
1               5                   10

<210> SEQ ID NO 31
<211> LENGTH: 8
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (5)..(5)
<223> OTHER INFORMATION: X represents D-Trp
<220> FEATURE:
<221> NAME/KEY: MISC_FEATURE
<222> LOCATION: (8)..(8)
<223> OTHER INFORMATION: X represents Ilys
<220> FEATURE:
<221> NAME/KEY: MISC_FEATURE
<222> LOCATION: (10)..(10)
<223> OTHER INFORMATION: X represents Pro-NHEt

<400> SEQUENCE: 31

Phe Trp Ser Tyr Xaa Leu Arg Xaa
1               5

<210> SEQ ID NO 32
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (5)..(5)
<223> OTHER INFORMATION: X represents N-Met-Tyr
<220> FEATURE:
```

```
<221> NAME/KEY: MISC_FEATURE
<222> LOCATION: (6)..(6)
<223> OTHER INFORMATION: X represents D-Lys-Nic
<220> FEATURE:
<221> NAME/KEY: MISC_FEATURE
<222> LOCATION: (8)..(8)
<223> OTHER INFORMATION: X represents Ilys
<220> FEATURE:
<221> NAME/KEY: MISC_FEATURE
<222> LOCATION: (10)..(10)
<223> OTHER INFORMATION: X represents D-Ala-NH2

<400> SEQUENCE: 32

Xaa Xaa Xaa Ser Xaa Xaa Leu Xaa Pro Xaa
1               5                   10

<210> SEQ ID NO 33
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (5)..(5)
<223> OTHER INFORMATION: X represents Aph (Hor), hydroorotyl
<220> FEATURE:
<221> NAME/KEY: MISC_FEATURE
<222> LOCATION: (6)..(6)
<223> OTHER INFORMATION: X represents D-Aph (Cpa)
<220> FEATURE:
<221> NAME/KEY: MISC_FEATURE
<222> LOCATION: (8)..(8)
<223> OTHER INFORMATION: X represents Ilys
<220> FEATURE:
<221> NAME/KEY: MISC_FEATURE
<222> LOCATION: (10)..(10)
<223> OTHER INFORMATION: X represents D-Ala-NH2

<400> SEQUENCE: 33

Xaa Xaa Xaa Ser Xaa Xaa Leu Xaa Pro Xaa
1               5                   10

<210> SEQ ID NO 34
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-4Cpa
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
```

```
<223> OTHER INFORMATION: X represents D-Lys
<220> FEATURE:
<221> NAME/KEY: MISC_FEATURE
<222> LOCATION: (10)..(10)
<223> OTHER INFORMATION: X represents D-Ala-NH2

<400> SEQUENCE: 34

Xaa Xaa Xaa Ser Tyr Xaa Leu Arg Pro Xaa
1               5                   10

<210> SEQ ID NO 35
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-4Cpa
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Arg
<220> FEATURE:
<221> NAME/KEY: MISC_FEATURE
<222> LOCATION: (10)..(10)
<223> OTHER INFORMATION: X represents D-Ala-NH2

<400> SEQUENCE: 35

Xaa Xaa Xaa Ser Tyr Xaa Leu Arg Pro Xaa
1               5                   10

<210> SEQ ID NO 36
<211> LENGTH: 10
<212> TYPE: PRT
<213> ORGANISM: homo sapiens
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (10)..(10)
<223> OTHER INFORMATION: Gly-NH2

<400> SEQUENCE: 36

Glu His Trp Ser Tyr Gly Leu Arg Pro Gly
1               5                   10

<210> SEQ ID NO 37
<211> LENGTH: 10
<212> TYPE: PRT
<213> ORGANISM: artificial sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
```

```
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Lys
<220> FEATURE:
<221> NAME/KEY: MISC_FEATURE
<222> LOCATION: (10)..(10)
<223> OTHER INFORMATION: X represents D-Ala-NH2

<400> SEQUENCE: 37

Xaa Xaa Xaa Ser His Xaa Trp Tyr Pro Xaa
1               5                   10

<210> SEQ ID NO 38
<211> LENGTH: 10
<212> TYPE: PRT
<213> ORGANISM: artificial sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Lys
<220> FEATURE:
<221> NAME/KEY: MISC_FEATURE
<222> LOCATION: (10)..(10)
<223> OTHER INFORMATION: X represents D-Ala-NH2

<400> SEQUENCE: 38

Xaa Xaa Xaa Ser His Xaa Trp Leu Pro Xaa
1               5                   10

<210> SEQ ID NO 39
<211> LENGTH: 10
<212> TYPE: PRT
<213> ORGANISM: artificial sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Lys
<220> FEATURE:
<221> NAME/KEY: MISC_FEATURE
<222> LOCATION: (10)..(10)
<223> OTHER INFORMATION: X represents D-Ala-NH2

<400> SEQUENCE: 39

Xaa Xaa Xaa Ser Tyr Xaa Trp Tyr Pro Xaa
```

<210> SEQ ID NO 40
<211> LENGTH: 10
<212> TYPE: PRT
<213> ORGANISM: artificial sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-Lys
<220> FEATURE:
<221> NAME/KEY: MISC_FEATURE
<222> LOCATION: (10)..(10)
<223> OTHER INFORMATION: X represents D-Ala-NH2

<400> SEQUENCE: 40

Xaa Xaa Xaa Ser Tyr Xaa Trp Leu Pro Xaa
1               5                   10

<210> SEQ ID NO 41
<211> LENGTH: 10
<212> TYPE: PRT
<213> ORGANISM: artificial sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-3Pal
<220> FEATURE:
<221> NAME/KEY: MISC_FEATURE
<222> LOCATION: (10)..(10)
<223> OTHER INFORMATION: X represents D-Ala-NH2

<400> SEQUENCE: 41

Xaa Xaa Xaa Ser His Xaa Trp Leu Pro Xaa
1               5                   10

<210> SEQ ID NO 42
<211> LENGTH: 10
<212> TYPE: PRT
<213> ORGANISM: artificial sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:

```
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-3Pal
<220> FEATURE:
<221> NAME/KEY: MISC_FEATURE
<222> LOCATION: (10)..(10)
<223> OTHER INFORMATION: X represents D-Ala-NH2

<400> SEQUENCE: 42

Xaa Xaa Xaa Ser Tyr Xaa Trp Tyr Pro Xaa
1               5                   10

<210> SEQ ID NO 43
<211> LENGTH: 10
<212> TYPE: PRT
<213> ORGANISM: artificial sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-3Pal
<220> FEATURE:
<221> NAME/KEY: MISC_FEATURE
<222> LOCATION: (6)..(6)
<223> OTHER INFORMATION: X represents D-3Pal
<220> FEATURE:
<221> NAME/KEY: MISC_FEATURE
<222> LOCATION: (10)..(10)
<223> OTHER INFORMATION: X represents D-Ala-NH2

<400> SEQUENCE: 43

Xaa Xaa Xaa Ser Tyr Xaa Trp Leu Pro Xaa
1               5                   10

<210> SEQ ID NO 44
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents D-2-Ome-5Pal
<220> FEATURE:
<221> NAME/KEY: MISC_FEATURE
<222> LOCATION: (5)..(5)
<223> OTHER INFORMATION: X represents 4-Aminophenylalanine L-hydroorotyl
<220> FEATURE:
<221> NAME/KEY: MISC_FEATURE
<222> LOCATION: (6)..(6)
```

```
<223> OTHER INFORMATION: X represents 4-Aminophenylalanine carbamoyl
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: X represents D-Ala-NH2

<400> SEQUENCE: 44

Xaa Xaa Xaa Ser Xaa Xaa Leu Xaa Pro Xaa
 1               5                  10

<210> SEQ ID NO 45
<211> LENGTH: 10
<212> TYPE: PRT
<213> ORGANISM: artificial sequence
<220> FEATURE:
<223> OTHER INFORMATION: GnRH I antagonist
<220> FEATURE:
<221> NAME/KEY: MISC_FEATURE
<222> LOCATION: (1)..(1)
<223> OTHER INFORMATION: X represents Ac-D-2Nal
<220> FEATURE:
<221> NAME/KEY: MISC_FEATURE
<222> LOCATION: (2)..(2)
<223> OTHER INFORMATION: X represents D-4Cpa
<220> FEATURE:
<221> NAME/KEY: MISC_FEATURE
<222> LOCATION: (3)..(3)
<223> OTHER INFORMATION: X represents L2-OMe-5Pal
<220> FEATURE:
<221> NAME/KEY: MISC_FEATURE
<222> LOCATION: (5)..(5)
<223> OTHER INFORMATION: X represents 4-aminophenylalanine L-hydroorotyl
<220> FEATURE:
<221> NAME/KEY: MISC_FEATURE
<222> LOCATION: (6)..(6)
<223> OTHER INFORMATION: X represents 4-aminophenylalanine carbamoyl
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: X represents D-Ala-NH2

<400> SEQUENCE: 45

Xaa Xaa Xaa Ser Xaa Xaa Leu Xaa Pro Xaa
 1               5                  10

<210> SEQ ID NO 46
<211> LENGTH: 10
<212> TYPE: PRT
<213> ORGANISM: artificial sequence
<220> FEATURE:
<223> OTHER INFORMATION: GnRH II antagonist
<220> FEATURE:
<221> NAME/KEY: MISC_FEATURE
<222> LOCATION: (1)..(1)
<223> OTHER INFORMATION: X can represent Ac-D-2Nal, Ac-delta3Pro
<220> FEATURE:
<221> NAME/KEY: MISC_FEATURE
<222> LOCATION: (2)..(2)
<223> OTHER INFORMATION: X can represent His, D-4Cpa, Arg, Tyr, Trp,
      D-4Fpa, D-4Bpa
<220> FEATURE:
<221> NAME/KEY: MISC_FEATURE
<222> LOCATION: (3)..(3)
<223> OTHER INFORMATION: X can represent Trp, D-3Pal, D-2Nal, Ala, Phe,
      His
<220> FEATURE:
<221> NAME/KEY: MISC_FEATURE
<222> LOCATION: (5)..(5)
```

```
<223> OTHER INFORMATION: X can represent Tyr, His
<220> FEATURE:
<221> NAME/KEY: MISC_FEATURE
<222> LOCATION: (6)..(6)
<223> OTHER INFORMATION: X can represent D-Lys, D-Trp, D-3Pal, D-2Nal
<220> FEATURE:
<221> NAME/KEY: MISC_FEATURE
<222> LOCATION: (7)..(7)
<223> OTHER INFORMATION: X can represent Trp, Leu, Arg
<220> FEATURE:
<221> NAME/KEY: MISC_FEATURE
<222> LOCATION: (8)..(8)
<223> OTHER INFORMATION: X can represent Tyr, Leu, Arg
<220> FEATURE:
<221> NAME/KEY: MISC_FEATURE
<222> LOCATION: (10)..(10)
<223> OTHER INFORMATION: X can represent D-Ala, D-Gly, D-Cys, D-Ser,
      D-Val, D-Thr, D-Pro, D-Ile, D-Leu

<400> SEQUENCE: 46

Xaa Xaa Xaa Ser Xaa Xaa Xaa Xaa Pro Xaa
1               5                   10
```

METHOD FOR INDUCTION AND ENHANCEMENT OF APOPTOSIS IN TUMOR CELLS

The present invention relates to methods for inducing and/or enhancing apoptosis in pathogenic cells. In particular, the present invention relates to the use of GnRH II antagonists for inducing and/or enhancing apoptosis of specific types of tumor cells, expressing the GnRH II receptor as well as to methods relating thereto.

BACKGROUND

The hypothalamic decapeptide gonadotropin-hormone-releasing hormone (GnRH), also known as lutenizing hormone-releasing-hormone (LHRH), functions as a key hormone in the regulation of mammalian reproduction. It is released from the hypothalamus and stimulates the synthesis and release of lutenizing hormone (LH) and follicle stimulating hormone (FSH). In addition to its classic hypophysiotropic action, GnRH functions as a modulator of the activity of diverse systems in the brain and many peripheral organs. It has been suggested that an autocrine/paracrine function of GnRH exists for example in the placenta, granulosa cells, myometrium and lymphoid cells. In addition, this GnRH based autocrine system seems to be present in a number of human malignant tumors including cancers of the ovary, endometrium, breast and other reproductive organs.

About 80% of the endometrial and ovarian cancers and about 50% of all breast cancers, and a large number of the malignant melanoma have GnRH receptors as part of their negative autocrine regulation system for cell proliferation. These types of cancer cells or tumor cells can also be identified as steroid-related or steroid-sensitive tumor cells. In normal tissue GnRH receptors are not present or only expressed very weakly.

The GnRH is a peptide and, today, various forms of the GnRH have been described. One type of GnRH is the mammalian GnRH (mGnRH or GnRH 1), which was first found in the mammalian hypothalamus. The second type of GnRH (GnRH 11) was described for the first time in chicken brain. GnRH II can be found in almost all vertebrates including mammalia. Beside the expression in the central nervous system the expression of GnRH-I and GnRH-II has been reported in tissues regulating the immune and reproductive system.

As mentioned above, it is known that the GnRH-I and its receptor represents a part of the negative autocrine regulation system for cell proliferation, of the cell cycle as well as in the anti-apoptosis system. The signalling pathway involved in the autocrine regulation system was studied in detail and it was demonstrated that GnRH-I via the nucleus factor kappa B (NF-κB) protects tumor cells from going into the apoptosis.

It was known that in tumor cells GnRH-I agonist and antagonist act in the same way, i.e. both display an anti-proliferative activity. That means, GnRH-I antagonists act like agonists indicating that the dichotomy of GnRH-I agonist and antagonist does not exist in tumor cells. Further, it is described that the anti-proliferative effect of the GnRH-I agonist can be abrogated in cells wherein the signalling pathway via the GnRH I receptor is interrupted. In contrast, the GnRH-I antagonist still has an anti-proliferative effect on this type of cells.

The exact amino acid sequence of the human GnRH-II receptor is not known, although various attempts have been made to clone the receptor and to obtain the complete nucleic acid sequence. Further, no successful characterization of the human GnRH-II receptor is given in the literature. The information known today about the GnRH-II receptor are based on data obtained from other mammalian species. For the human receptor, no functional transcript is described.

Agonists and antagonists of the GnRH type II molecules of non human mammalian species are described in the art. For example, WO 00/32218 describes pharmaceutical formulations containing GnRH II and antagonists thereof. In WO 03/093304 various agonists and antagonists of the GnRH II are disclosed useful for the treatment of reproductive physiology diseases and steroid-related cancer cells. It was demonstrated that the anti-proliferative effects of GnRH type II agonists as well as of the native GnRH II is higher than the anti-proliferative effect demonstrated for the GnRH I analoga.

It was known that GnRH I and GnRH II as well as GnRH I analoga and GnRH II agonists are able to influence the proliferation of tumor cells. That is, these molecules can decrease the proliferation rate of the tumor cells, thereby stopping or reducing the growth of the tumor. However, the ultimate goal in tumor treatment, the full disappearance of the tumor, i.e. the full remission of the tumor, can not be achieved when stopping the proliferation of the tumor cells only. More importantly, it is necessary that the tumor and all pathogenic cells whether present in the solid tumor or present as dissimilated cells, are removed e.g. by killing the tumor cells. Thus, full remission can be achieved. Typically, the removal of pathogenic cells may be obtained by surgery or by the induction of cell death. It is well known that the abnormal inhibition of apoptosis is a hallmark of cancer or other diseases. That is, it is desirable to treat tumor diseases not only by stopping the proliferation of tumor cells but also by inducing cell death of the tumor cells. A possibility to drive cell into the cell death is to induce the cell death program by apoptosis.

Thus, one object of the present invention is to provide a method for inducing or enhancing the apoptosis of tumor cells or precursor cells thereof of breast cancer and malignant melanoma.

In an another aspect, the present invention relates to a method for inducing or enhancing the apoptosis of tumor cells or precursor cells thereof of gynaecological cancers, like endometrial cancer or ovarian cancer. Furthermore, the present invention aims to provide a method for reducing the number of tumor cells and precursor cells thereof.

In addition, the present invention provides GnRH II antagonists being superior over the hitherto described GnRH II antagonists in view of their activity and their capacity of enhancing apoptosis in tumor cells.

SUMMARY OF THE INVENTION

The present invention is directed, in part, to the novel and unexpected finding that GnRH II antagonists can induce and/or enhance apoptosis in tumor cells or precursor cells thereof of specific types of cancers, expressing the GnRH II receptor.

Hence, the present invention provides for methods for inducing and/or enhancing apoptosis of pathogenic cells, like in tumor cells or precursor cells thereof of specific types of tumors expressing the GnRH II receptor.

Further, the present invention provides for methods for reducing the number of pathogenic cells, thus, reducing e.g. the tumor size, in particular for the full remission of tumor cells of specific types of cancers.

In addition, the present invention is concerned with the use of GnRH I antagonists and GnRH II antagonists or derivatives thereof in pharmaceutical compositions for inducing and/or enhancing apoptosis in tumor cells or precursor cell thereof of specific types of cancer expressing the GnRH II receptor.

In some embodiments, the induction and/or enhancement of apoptosis in pathogenic cells, like tumor cells, is achieved by contacting the cells with GnRH II antagonist(s) or derivatives thereof. In a preferred embodiment, said GnRH II antagonists are peptides having a sequence according to SEQ ID NO. 1.

That is, the present invention is particularly useful for the treatment of breast cancer and various forms of malignant melanoma. Further, the present invention is particularly useful for the treatment of gynaecological cancers.

Finally, the present invention concerns new GnRH II antagonists particularly useful and more potential in the treatment of tumors comprising cancer cells expressing the GnRH II receptor, in particular of gynaecological tumors and tumors of reproductive organs as well as breast cancer and malignant melanoma.

Western blot analysis of cell membrane preparations of ovaries obtained from marmoset monkey under reducing conditions yielded a band at approximately 54 kDa (C).

Figure 1:
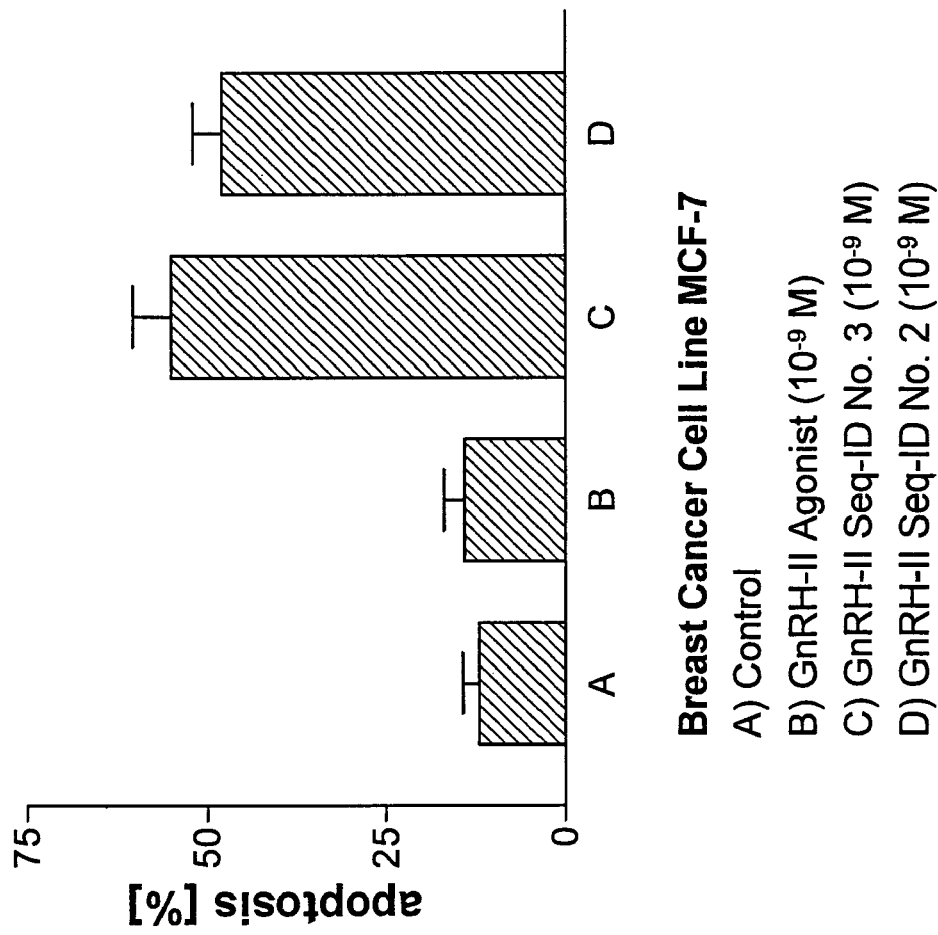
FIG. 1 shows a flow cytometric analysis of breast cancer cell line MCF-7 as described in the Examples. After 72 h of treatment with $10^{-9}$ M of the GnRH-II antagonists with Seq.-ID No. 3 (C) or Seq.-ID No. 2 (D), characteristic apoptotic DNA degradation was observed. GnRH-II agonist [D-Lys$^6$]GnRH-II did not induce apoptotic cell death (B).
Figure 2:
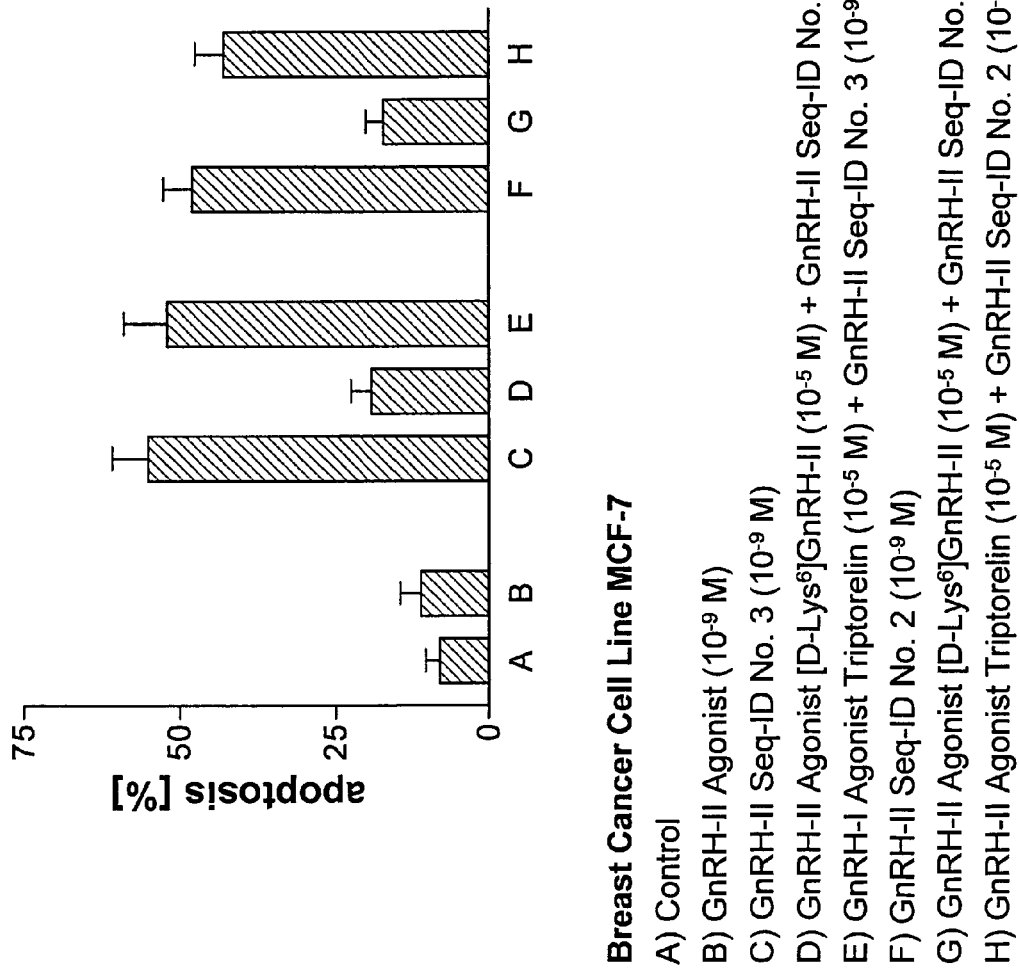
FIG. 2 shows a flow cytometric analysis of breast cancer cell line MCF-7. After 72 h of treatment with $10^{-9}$ M of the GnRH-II antagonists with Seq.-ID No. 3 (C) or Seq.-ID No. 2 (F), characteristic apoptotic DNA degradation was observed. After 72 h of treatment with $10^{-9}$ M of GnRH-II antagonists with Seq-ID No. 3 or Seq.-ID No. 2 in the presence of $10^{-5}$ M of GnRH-II agonist [D-Lys$^6$]GnRH-II, a significantly lower amount of characteristic apoptotic DNA degradation was observed (D, G). Co-treatment with GnRH-I agonist Triptorelin showed only a slight decrease of apoptotic cells (E, H).
Figure 3:
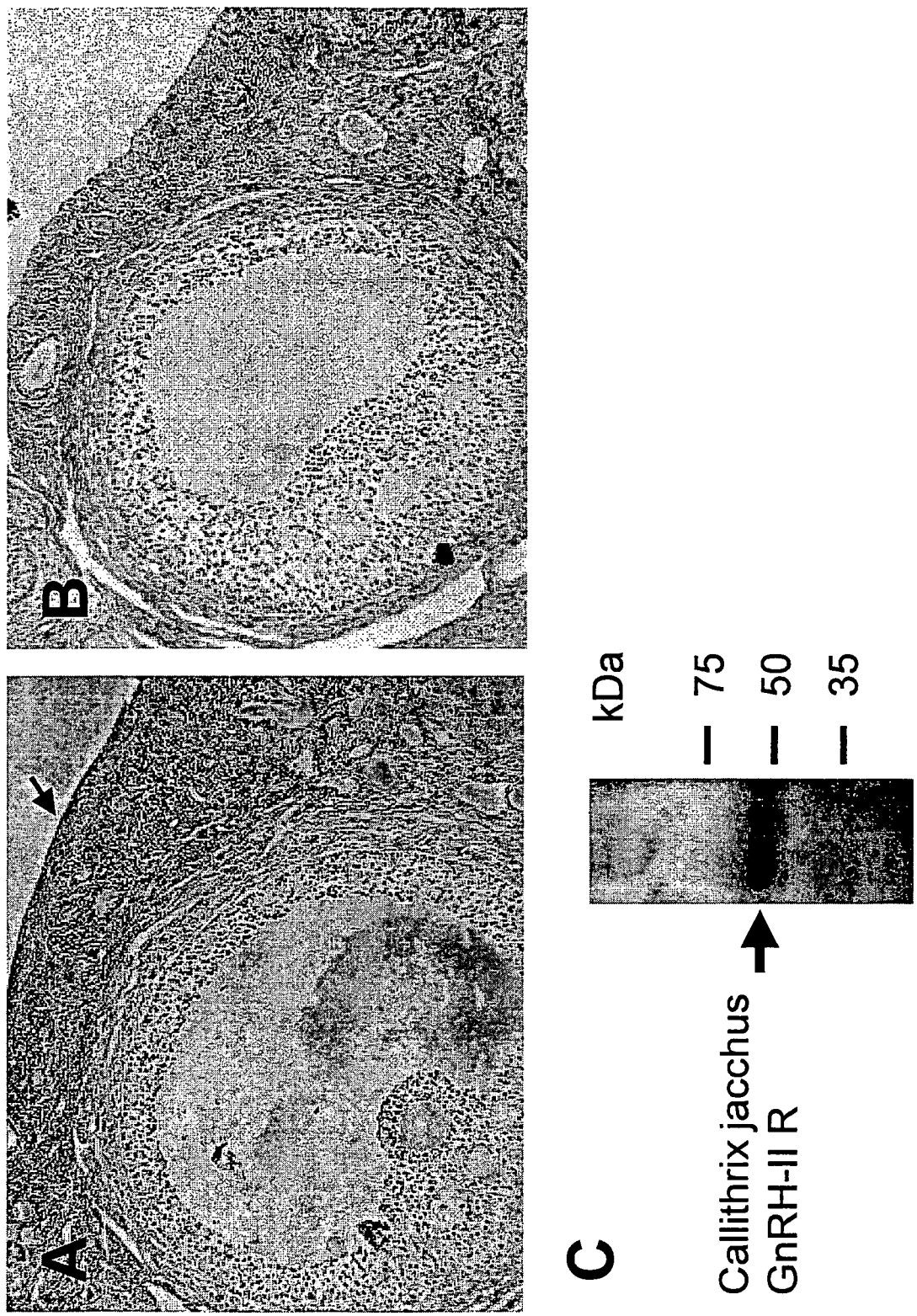
FIG. 3 demonstrates the GnRH-II receptor expression in the ovary of the marmoset monkey. Immune histochemical localization of GnRH-II receptor antigenicity in ovaries obtained from marmoset monkey (A). The most intensive staining was shown in the surface epithelium of the ovary (Arrow). Controls performed by substitution of the primary antiserum with pre-immune serum of the same rabbit showed no staining (B).
Figure 4:
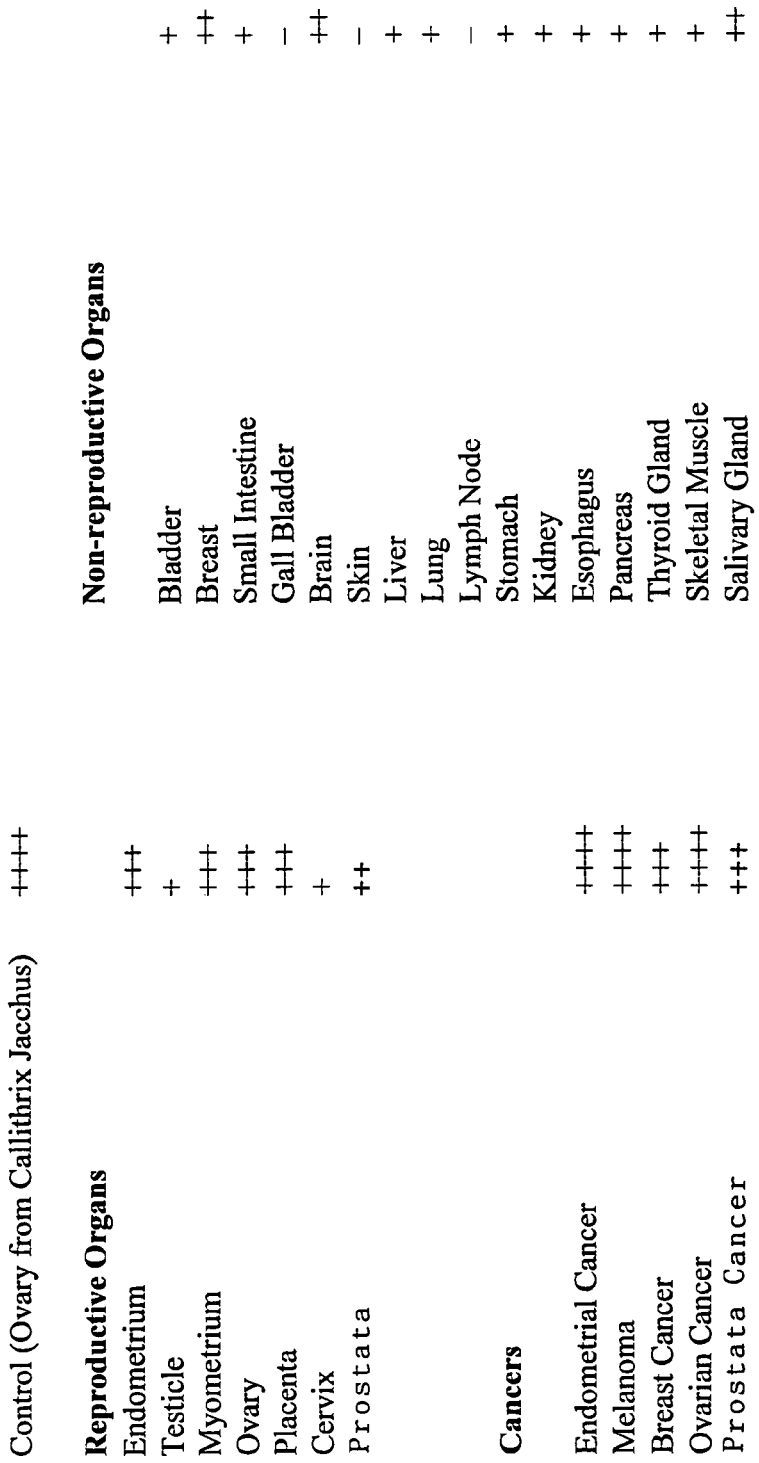

FIG. 4 shows the immune histological detection of GnRH-II receptor antigenicity in reproductive and non-reproductive human tissues as well as in specific type of cancers using anti GnRH-II receptor antiserum mentioned in the experimental section.

Figure 5:
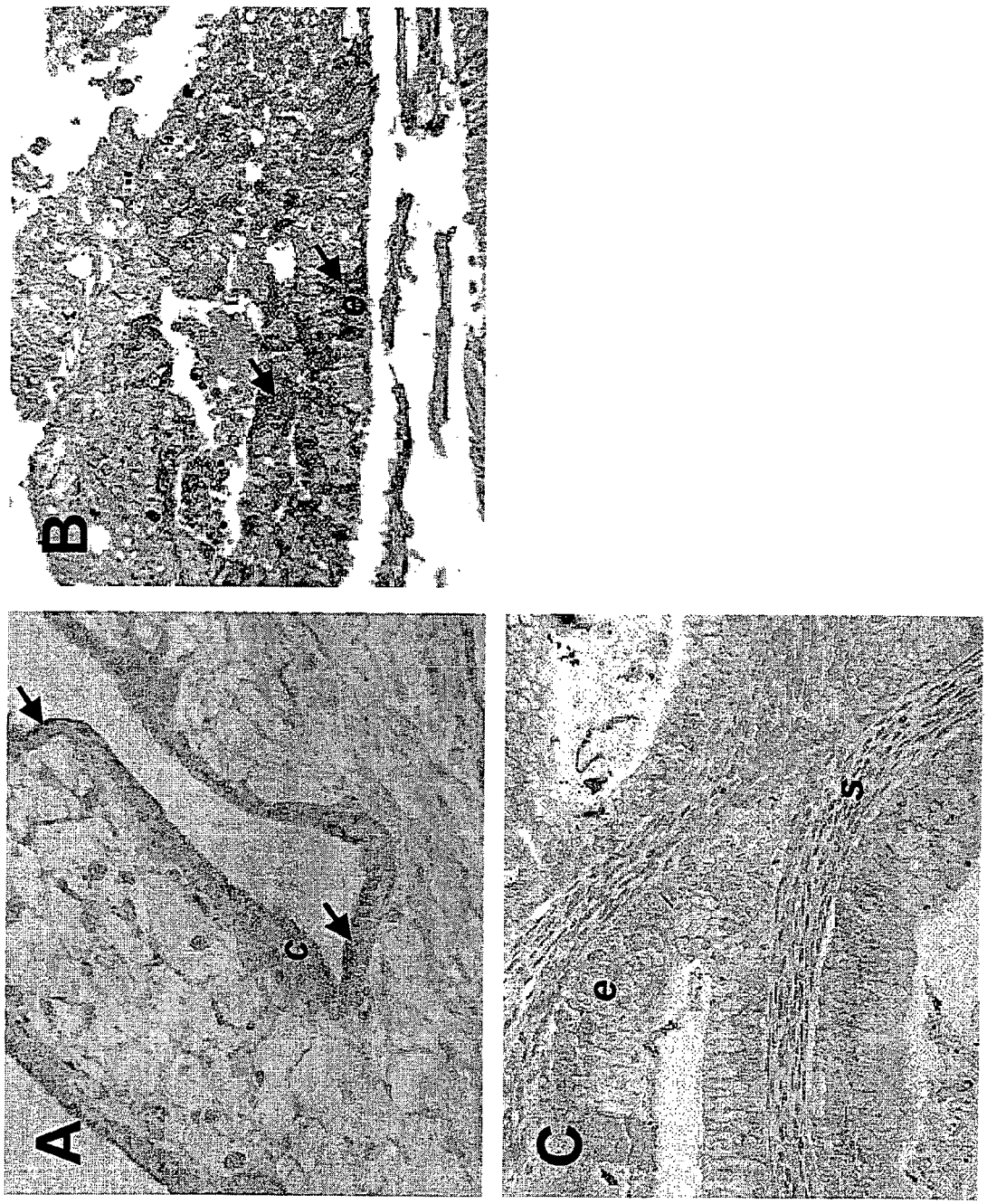

FIG. 5 demonstrates the immune histochemical localization of GnRH-II receptor antigenicity in sections of human placenta (gestational age: twenty-fifth week) (A), a human endometrial adenocarcinoma (B), and a human mucinous cystadenocarcinoma of the ovary (C). p placental chorionic epithelial cells; s stromal cells; e epithelial cells.

Figure 6:
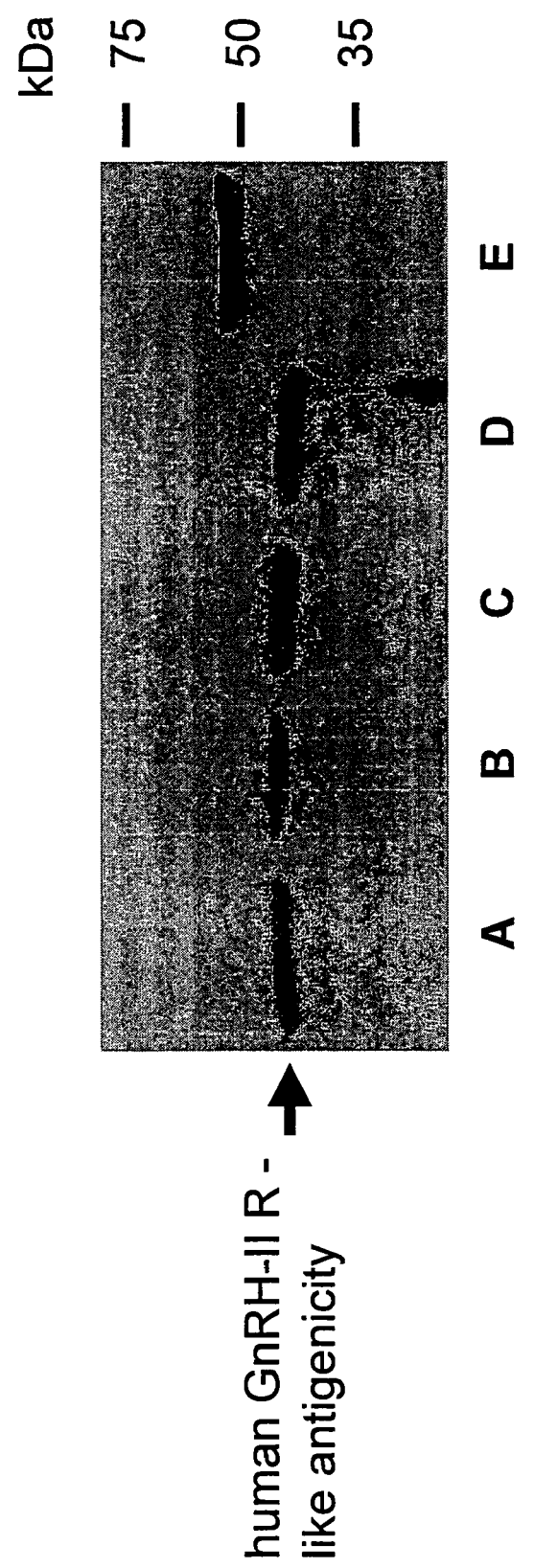

FIG. 6 is a Western Blot of the GnRH II receptor expression in human cell lines. The GnRH-II receptor-like protein expression in cell membrane preparations of human endometrial cancer cell lines Ishikawa (A) and Hec-1A (B) and human ovarian cancer cell lines EFO-21 (C) and SK—OV-3 (D) is shown. GnRH-II receptor protein expression in cell membrane preparations of ovaries obtained from marmoset monkey is shown in (E).

The data were obtained from three independent experiments run in duplicate in three different passages of each cell line. The experiments using ovaries from marmoset monkey were repeated four times using four different ovaries obtained from two different animals.

Figure 7:
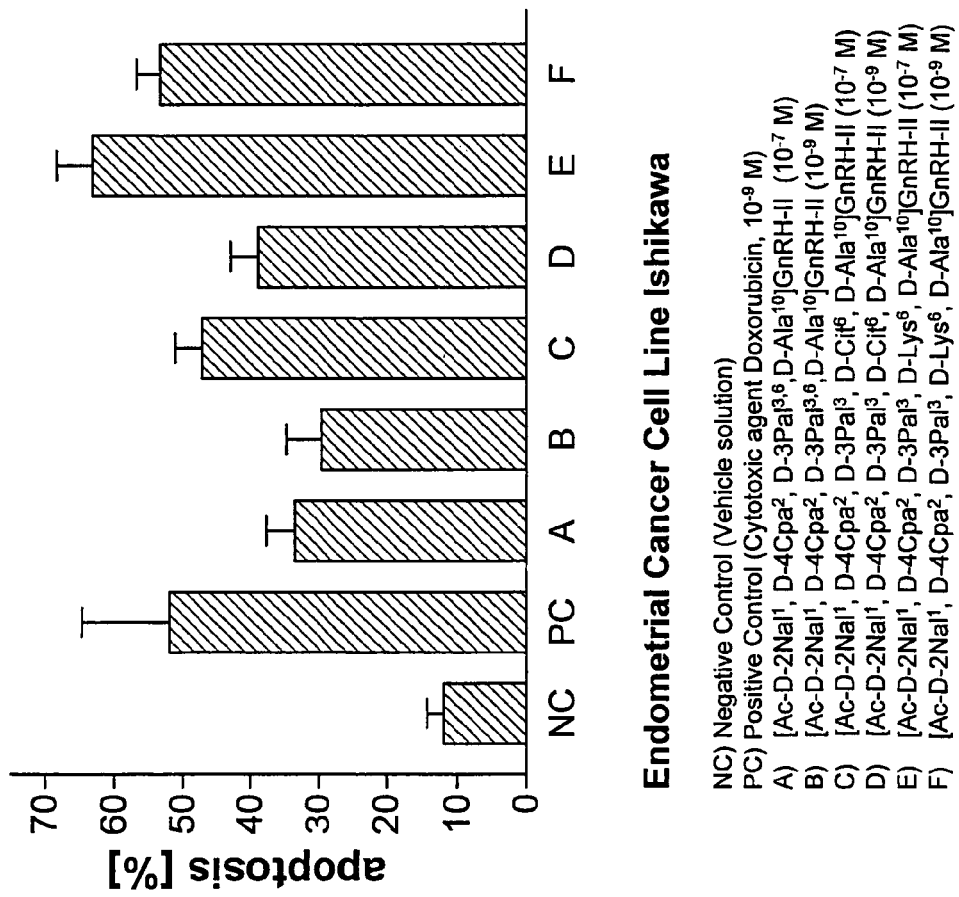

FIG. 7 illustrates the induction of apoptosis in the endometrial cell line Ishikawa. NC denotes negative control, i.e. vehicle solution only. PC means positive control, cytotoxic agent Doxorubicin, $10^{-9}$ M. A and B are different concentrations ($10^{-7}$ M and $10^{-9}$ M, respectively) of the GnRH II antagonist according to Seq ID No. 2. C and D are different concentrations ($10^{-7}$ M and $10^{-9}$ M, respectively) of the GnRH II antagonist according to Seq ID No. 9. E and F are different concentrations ($10^{-7}$ M and $10^{-9}$ M, respectively) of the GnRH II antagonist according to Seq ID No. 37.

Figure 8:
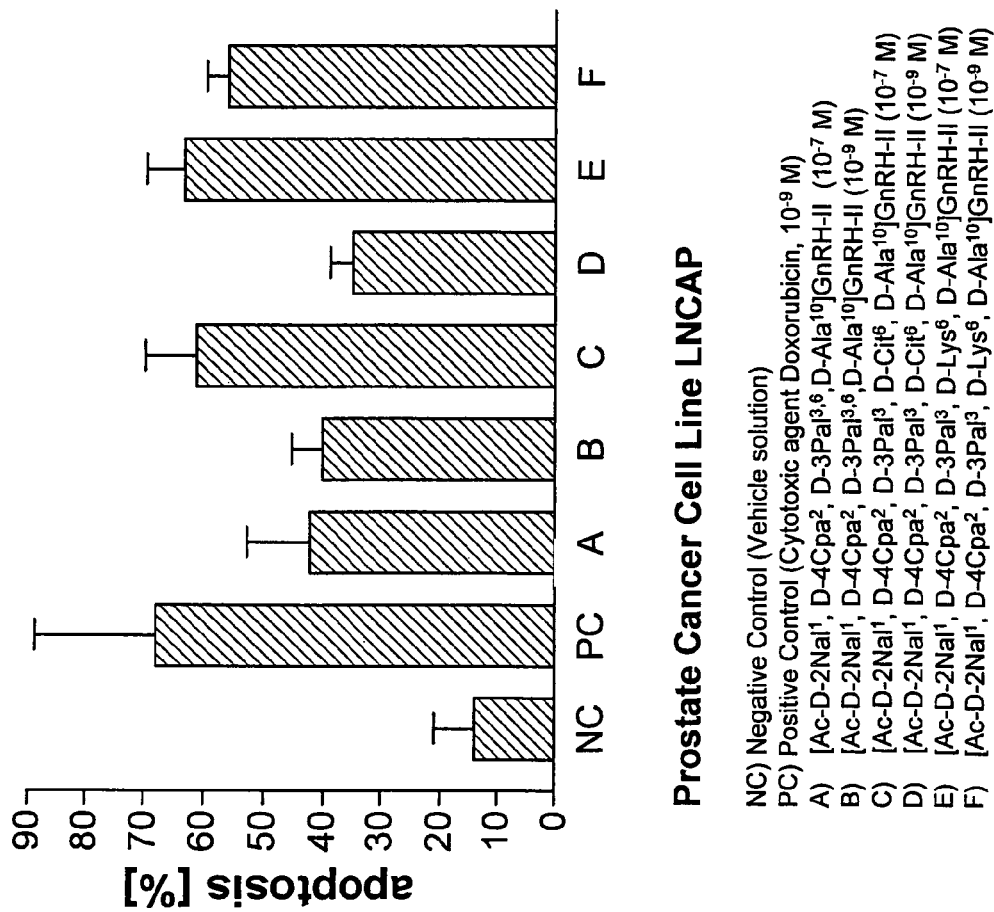

FIG. 8 demonstrates the induction of apoptosis in the prostate cancer cell line LNCAP. NC denotes negative control, i.e. vehicle solution only. PC means positive control, cytotoxic agent Doxorubicin, $10^{-9}$ M. A and B are different concentrations ($10^{-7}$ M and $10^{-9}$ M, respectively) of the GnRH II antagonist according to Seq ID No. 2. C and D are different concentrations ($10^{-7}$ M and $10^{-9}$ M, respectively) of the GnRH II antagonist according to Seq ID No. 9. E and F are different concentrations ($10^{-7}$ M and $10^{-9}$ M, respectively) of the GnRH II antagonist according to Seq ID No. 37.

Figure 9:
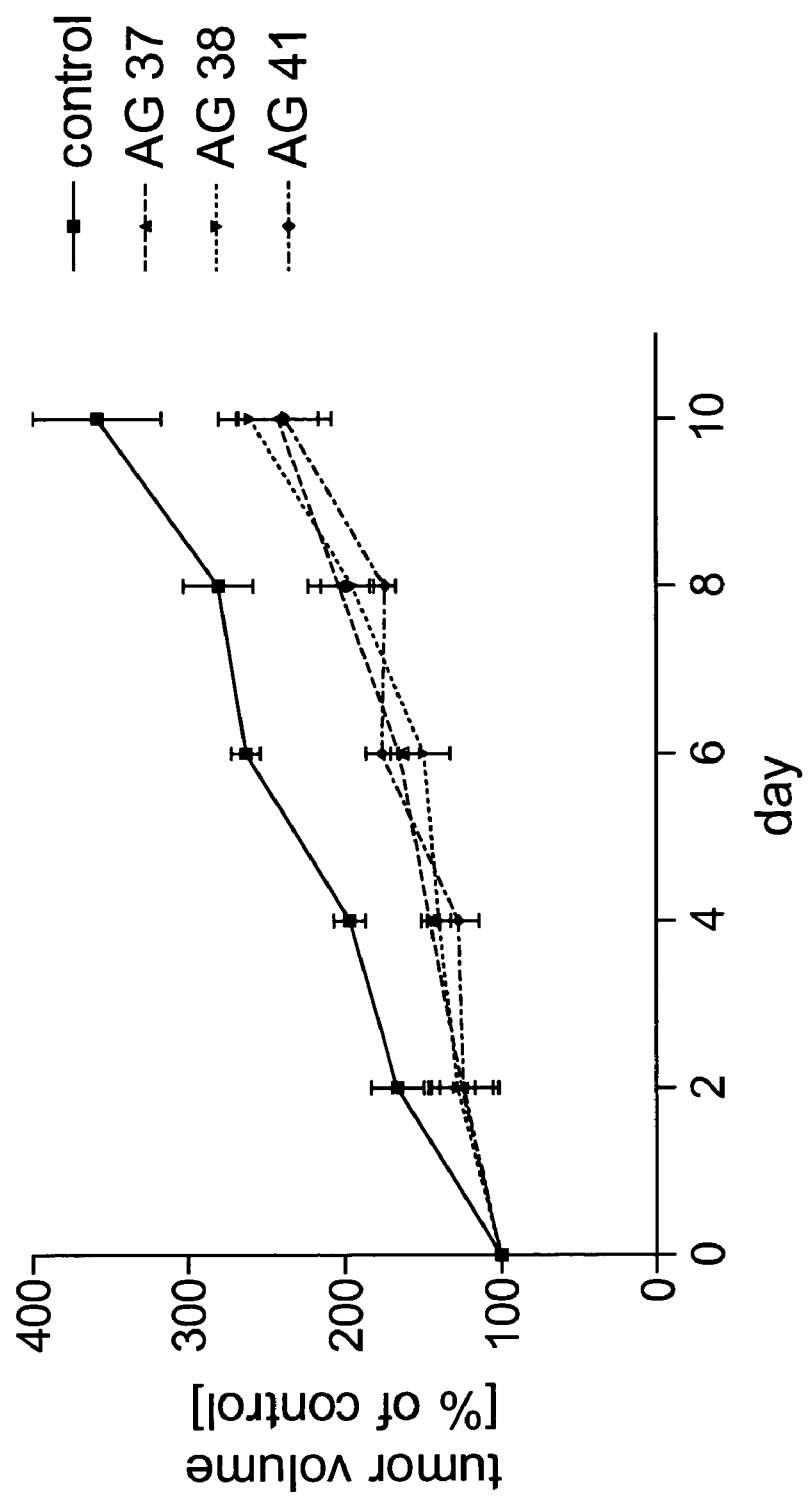

FIG. 9 shows the evaluation of GnRH-II antagonists on human ovarian cancers xenografted into nude mice. The mice were treated without (control) or with 25 nmol of GnRH-II antagonists with Seq. ID No. 37, Seq. ID No. 38, and Seq. ID No. 41, respectively. Treatment was repeated every day.

Figure 10:
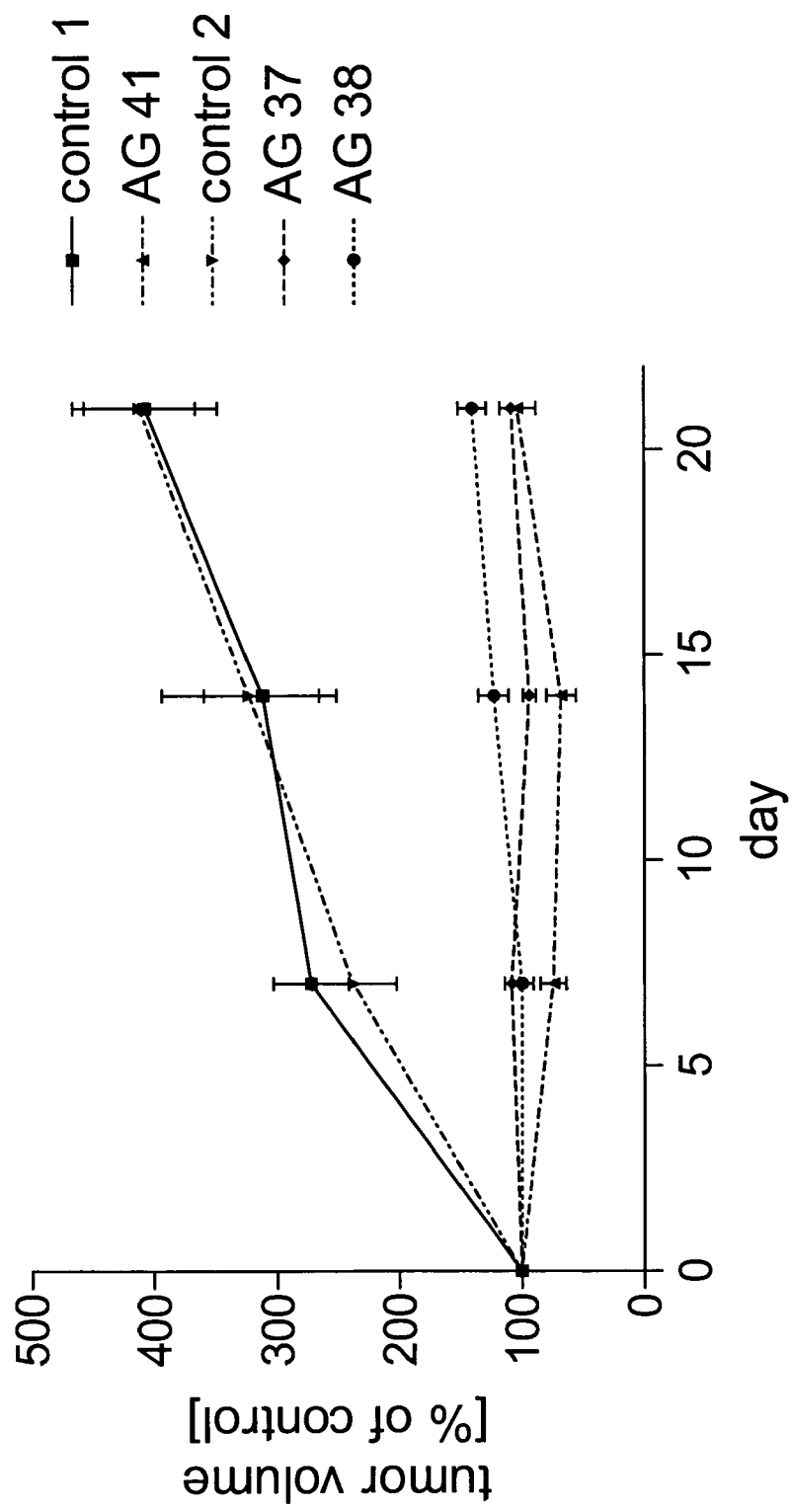

FIG. 10 shows the tumor volume of human endometrial cancers xenografted into nude mice. Treatment was conducted without (control 1) or with GnRH-I agonist Triptorelin (control 2) or with 25 nmol of GnRH-II antagonists with Seq. ID No. 37, Seq. ID No. 38, and Seq. ID No. 41, respectively. Intraperitoneally injection was repeated every 2 days.

Figure 11:
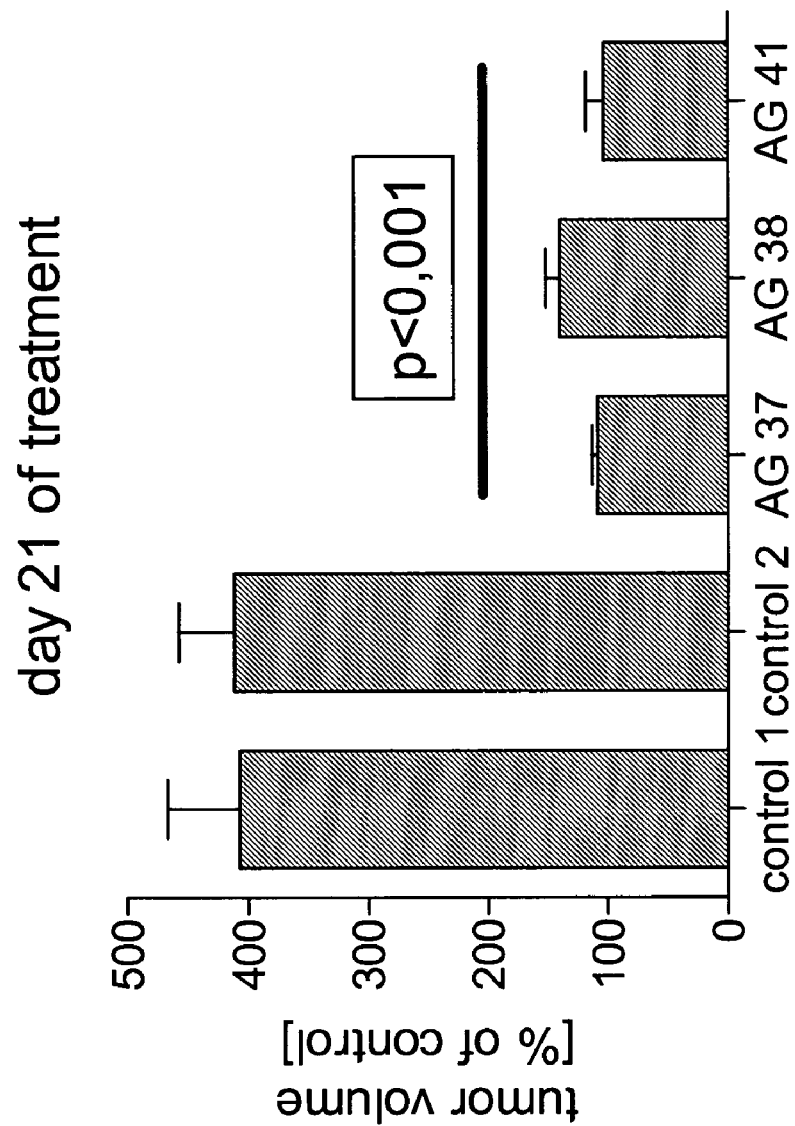

FIG. 11 demonstrates the tumor volume of human endometrial cancers xenografted into nude mice on day 21 of treatment. reatment without (control 1) or with GnRH-I agonist Triptorelin (control 2) or with 25 nmol of GnRH-II antagonists with Seq. ID No. 37, Seq. ID No. 38, and Seq. ID No. 41, respectively. Intraperitoneally injection was repeated every 2 days.

DETAILED DESCRIPTION OF THE PRESENT INVENTION

The following description of particular embodiments and examples are offered by way of illustration and not by way of limitation. Unless contraindicated or noted otherwise in these descriptions and throughout the specification, the terms "a" and "an" mean one or more, the term "and/or" when occurring herein includes the meaning of "and", "or" and "all or any other combination of the elements connected by said term".

The following definitions are set forth to illustrate and define the meaning and scope of the various terms used to describe the invention herein.

"Agonist" refers to a biologically active ligand which binds to its complementary biologically active receptor and activates the latter either to cause a biological response in the receptor or to enhance pre-existing biological activity of the receptor.

"Antagonists" refers to a biologically active ligand which binds to its complementary biologically active receptor and does not activate the latter to cause the natural biological response in the receptor or to reduce pre-existing biological activity of the receptor.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is H is or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G: Additionally, Ac-(D)-2Nal is Acetyl-β-(2-Naphthyl)-(D)-Alanine; Ac-Δ³Pro is Acetyl-3, 4-dehydro-Proline; D-4 Cpa [=(4Cl)-D-Phe] is 4-Chloro-D-Phenylalanine; D-4Fpa [=(4F)-D-Phe] is 4-Fluoro-D-Phenylalanine; D-4 Bpa [=(4Br)-D-Phe] is 4-Bromo-D-Phenylalanine; D-2 Pal is β-(2-Pyridyl)-D-Alanine; D-3 Pal is β-(3-Pyridyl)-D-Alanine; D-2Nal is β-(2-Naphthyl)-D-Alanine; D-Cit is D-Citrulline.

Unless otherwise specifically mentioned, the amino acid residues may be present in its D-form or L-form. Preferred the amino acid residues are in the L-form unless the D-form is specifically identified.

In addition to peptides consisting only of naturally-occurring L- or D-amino acids, peptide mimetics, also known as peptidomimetics or peptide analogs are also provided. Peptide analogs are commonly used in the pharmaceutical industry as non-peptide drugs with properties analogous to those of the template peptide. These types of compound are termed "peptide mimetics" or "peptidomimetics" (Fauchere, J. *Adv. Drug Res.* 15__29 (1986); Veber and Freidinger *TINS* p. 392 (1985); and Evans et al. *J. Med. Chem.* 30__1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH═CH (cis and trans), —COCH$_2$—, —CH(OH)CH$_2$—, and —CH$_2$SO—, by methods known in the art.

With derivatives of the GnRH II antagonists are meant all kind of peptides and/or proteins and/or fragments thereof, including peptides and/or proteins comprising posttranslational modifications, chemical modifications, enzymatic modifications and modifications due to other mechanisms. In particular, derivatives which do not negatively affect the properties of the GnRH II antagonists as described herein. Derivatives of peptides may comprise amino acid residues different from the standard set of 20 amino acids and/or may comprise peptidomimetic structures. Generally, the term "antagonist(s)" as used herein encompasses also derivatives of said antagonist(s).

The term "gynecological cancers" as used herein refers to cancers derived from tissues of the female reproductive tract such as ovary, fallopian tube, uterus (Endometrium, Myometrium), cervix.

The term "pathogenic cells" as used herein refers to cells which are neoplastic, e.g. tumor cells and precursor cells thereof.

The present inventors surprisingly found that specifically GnRH II antagonists not only have anti-proliferative activity, thus, stopping or decelerating tumor growth but also demonstrates an apoptosis inducing activity, thus, driving the tumor cells into the cell death by starting the cell death program. Consequently, full remission of the tumor may be achievable when applying a GnRH II antagonist treatment. This is even more surprising since the art discusses the use of superagonists as a potent agent for inhibiting tumor cell growth and tumor regression. A possible role of GnRH-II antagonists in tumor regression is neither disclosed nor envisaged in the art.

That is, the present invention provides methods for inducing and/or enhancing apoptosis in pathogenic cells expressing the GnRH II receptor comprising the step of contacting said cells with a GnRH II receptor antagonist or derivatives thereof.

In particular, the present invention is useful in the treatment of specific types of cancer, like breast cancer and/or malignant melanoma. Furthermore, the present invention is useful in the treatment of gynaecological cancers, particularly of ovarian or endometrial cancer.

Especially for malignant melanoma it was not known that said type of cancer express the GnRH receptor, particularly the GnRH II receptor. The expression of the GnRH II receptor on cancer cells of the malignant melanoma is surprising since this type of cells does not represent cells derived from tissue involved in the mammalian reproduction system.

In addition, specific GnRH II antagonists are disclosed being particularly useful in treating all types of cancer expressing the GnRH II receptor including but not limited to the above mentioned types of cancer, but also prostate cancer etc.

Thus, the present invention relates to a method of administering GnRH II antagonists or derivatives thereof, in particular, GnRH II antagonists having the sequence of Seq. ID No. 1, to a subject suffering from cancer, in particular of the specific types of cancer as mentioned herein. The GnRH II antagonists may be administered as pharmaceutical compositions known in the art. The pharmaceutical composition contains at least one GnRH II antagonist or derivatives thereof but also may contain at least two different GnRH II antagonists. The GnRH II antagonists are particularly useful in cancer therapy, preferably of the specific types of cancer mentioned herein.

Hence, in a further aspect, the present invention relates to pharmaceutical compositions comprising GnRH II antagonist(s) or derivatives thereof and, optionally, a pharmaceutically acceptable carrier.

In particular, the pharmaceutical composition comprises a compound having the general formula (Seq.-ID No. 46):

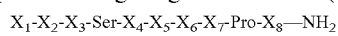

$X_1$-$X_2$-$X_3$-Ser-$X_4$-$X_5$-$X_6$-$X_7$-Pro-$X_8$—NH$_2$ wherein
X1=Ac-D-2Nal, Ac-Δ³Pro
X2=His, D-4 Cpa, Arg, Tyr, Trp, D-4Fpa, D-4 Bpa
X3=Trp, D-3 Pal, D-2Nal, Ala, Phe, His
X4=Tyr, His
X5=D-Lys, D-Trp, D-3 Pal, D-2Nal
X6=Trp, Leu, Arg
X7=Tyr, Leu, Arg
X8=D-Ala, D-Gly, D-Cys, D-Ser, D-Val, D-Thr, D-Pro, D-Ile, D-Leu or derivatives thereof as an active ingredient, optionally together with a pharmaceutically acceptable carrier. Preferably, The active ingredient is a compound according to Seq. ID No. 46 wherein X1 is Ac-D-2Nal, X2 is D-4-Cpa, D-4-Fpa or D-4 Bpa, X3 is D-3 Pal, X5 is D-Lys or D-3 Pal, X6 is Trp, X7 is Tyr or Leu and X8 is D-Ala. Particular preferred the active ingredient in the pharmaceutical composition is a compound selected from the group of Seq. ID. Nos. 37 to 43.

The pharmaceutical compositions comprise a therapeutically effective amount of the GnRH II antagonist(s) and, optionally, a pharmaceutically acceptable carrier. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium, carbonate, etc. Examples of suitable pharmaceutical carriers are described in "Remington's Pharmaceutical Sciences" by E. W. Martin ($18^{th}$ ed., Mack Publishing Co., Easton, Pa. (1990)). Such compositions will contain a therapeutically effective amount of the aforementioned GnRH II antagonist or its derivatives, preferably in purified form, together with a suitable amount of carrier so as to provide the form for proper administration to the patient. The formulation should suit the mode of administration.

Typically, pharmaceutically or therapeutically acceptable carrier is a carrier medium which does not interfere with the effectiveness of the biological activity of the active ingredients and which is not toxic to the host or patient.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in a unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition for use in connection with the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve a decrease in the immunological and/or inflammatory responses to infection or tissue injury.

In vitro assays may optionally be employed to help identifying optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

In the context of the present invention the term "subject" means an individual in need of a therapy that can be alleviated or cured by administering the GnRH II antagonist(s) to the individual. Preferably, the subject is a vertebrate, even more preferred a mammal, particularly preferred a human.

The term "administered" means administration of a therapeutically effective dose of the aforementioned pharmaceutical composition comprising the GnRH II antagonist(s) to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of ways as discussed above, including, but not limited to, orally, subcutaneously, intravenously, intraarterial, intranodal, intramedullary, intrathecal, intraventricular, intranasally, intrabronchial, transdermally, intrarectally, intraperitoneally, intramuscularly, intrapulmonary, vaginally, rectally, or intraocularly. In some instances, for example, in the treatment of wounds and inflammation, the pharmaceutically effective agent may be directly applied as a solution dry spray.

The attending physician and clinical factors will determine the dosage regimen. A typical dose can be, for example, in the range of 0.001 to 1000 µg; however, doses below or above this exemplary range are envisioned, especially considering the aforementioned factors.

In a preferred embodiment the GnRH II antagonist additionally may display GnRH I antagonist activity. The present inventors found that the unusual behaviour of GnRH I antagonists on tumor cells, the anti-proliferative effect may be based on the cross-reactivity with the GnRH II receptor. Thus, on cells not expressing the GnRH I receptor the GnRH I antagonist has an anti-proliferative activity. This kind of activity may be due to the presence of the GnRH II receptor on said cells.

In another preferred embodiments of the present invention the GnRH II antagonist is a peptide having the general sequence as shown below (SEQ ID No. 1)

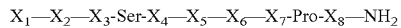
$X_1-X_2-X_3\text{-Ser-}X_4-X_5-X_6-X_7\text{-Pro-}X_8-NH_2$ wherein
X1=Ac-D-2Nal, Ac-2Nal, Ac-Δ³Pro
X2=His, D-4 Cpa, D-4Fpa, D-4 Bpa, Arg, Tyr, Trp,
X3=Trp, D-3 Pal, D-2Nal, Ala, Phe, His
X4=Tyr, His
X5=Gly, D-Lys, D-Cit, D-Trp, D-3 Pal, D-2Nal
X6=Trp, Leu, Arg
X7=Tyr, Leu, Arg
X8=Gly, Ala, D-Ala, D-Gly, D-Cys, D-Ser, D-Val, D-Thr, D-Pro, D-Ile, D-Leu
or derivatives thereof.

Particularly preferred embodiments are shown in tables 1 and 2, below.

Further preferred are peptides wherein X5 is D-Lys, D-3 Pal or D-Trp and X8 is D-Ala.

Table 1 shows decapeptides derived from the natural GnRH II peptide which is SEQ ID NO 18, corresponding to database entry Acc. No. o43555. Some of the peptides are disclosed in WO 00/32218 and WO 03/093304, respectively.

GnRH-II Antagonists

| SEQ ID NO | | | | | | | | | | |
|---|---|---|---|---|---|---|---|---|---|---|
| 18 | pGlu | His | Trp | Ser | His | Gly | Trp | Tyr | Pro | Gly-NH$_2$ |
| 2 | Ac-D-2Nal | D-4Cpa | D-3Pal | | | D-3Pal | | | | D-Ala-NH$_2$ |
| 3 | Ac-Δ³Pro | D-4Cpa | D-2Nal | | | D-2Nal | | | | D-Ala-NH$_2$ |
| 4 | Ac-D-2Nal | D-4Cpa | D-3Pal | | | D-2Nal | | | | |
| 5 | Ac-D-2Nal | D-4Cpa | D-3Pal | | | D-Cit | | | | |
| 6 | Ac-D-2Nal | D-4Cpa | D-3Pal | | | D-Lys | | | | |
| 7 | Ac-D-2Nal | D-4Cpa | D-3Pal | | | D-Trp | | | | |
| 8 | Ac-D-2Nal | D-4Cpa | D-3Pal | | Tyr | D-Cit | | | | D-Ala-NH$_2$ |
| 9 | Ac-D-2Nal | D-4Cpa | D-3Pal | | | D-Cit | | | | D-Ala-NH$_2$ |
| 10 | Ac-D-2Nal | D-4Cpa | D-3Pal | | Tyr | D-Cit | | | Leu | D-Ala-NH$_2$ |
| 11 | Ac-D-2Nal | D-4Cpa | Ala | | | D-Lys | | | | |
| 12 | Ac-D-2Nal | D-4Cpa | Phe | | | D-Lys | | | | |
| 13 | Ac-D-2Nal | D-4Cpa | His | | | D-Lys | | | | |
| 14 | Ac-D-2Nal | (4Cl)-D-Phe | D-3Pal | | | D-Lys | | | | |
| 15 | Ac-D-2Nal | Arg | D-3Pal | | | D-Lys | | | | |
| 16 | Ac-D-2Nal | Tyr | D-3Pal | | | D-Lys | | | | |
| 17 | Ac-D-2Nal | Trp | D-3Pal | | | D-Lys | | | | |
| 37 | Ac-D-2Nal | D-4Cpa | D-3Pal | | | D-Lys | | | | D-Ala-NH$_2$ |
| 38 | Ac-D-2Nal | D-4Cpa | D-3Pal | | | D-Lys | | | Leu | D-Ala-NH$_2$ |
| 39 | Ac-D-2Nal | D-4Cpa | D-3Pal | | Tyr | D-Lys | | | | D-Ala-NH$_2$ |
| 40 | Ac-D-2Nal | D-4Cpa | D-3Pal | | Tyr | D-Lys | | | Leu | D-Ala-NH$_2$ |
| 41 | Ac-D-2Nal | D-4Cpa | D-3Pal | | | D-3Pal | | | Leu | D-Ala-NH$_2$ |
| 42 | Ac-D-2Nal | D-4Cpa | D-3Pal | | Tyr | D-3Pal | | | | D-Ala-NH$_2$ |
| 43 | Ac-D-2Nal | D-4Cpa | D-3Pal | | Tyr | D-3Pal | | | Leu | D-Ala-NH$_2$ |

In another embodiment, the peptides and compounds shown in table 2 and derivatives thereof can be used in the methods according to the present invention. The peptides and compounds provided in table 2 represent peptides known in the art as GnRH I antagonists. Now it has been found that the GnRH I antagonists shown in table 2 may demonstrate a GnRH II antagonistic activity as well.

TABLE 2

| SEQ ID NO | | | | | | | | | | |
|---|---|---|---|---|---|---|---|---|---|---|
| 36 | GnRH-I | pGlu | His | Trp | Ser | Tyr | Gly | Leu | Arg | Pro | Gly-NH$_2$ |
| 19 | Abarelix | Ac-D-2Nal | D-4Cpa | D-3Pal | Ser | N-Me-Tyr | D-Asn | Leu | Ilys | Pro | D-Ala-NH$_2$ |
| 20 | Acyline | Ac-D-2NAl | D-4Cpa | D-3Pal | Ser | Aph (Ac) | D-Aph (Ac) | Leu | Ilys | Pro | D-Ala-NH$_2$ |
| 21 | Antarelix | N-Ac-DNal | D-4Cpa | D-3Pal | Ser | Tyr | D-(Hci) | Leu | Ilys | Pro | D-Ala-NH$_2$ |
| 22 | Antide (Iturelix) | Ac-D-2Nal | D-4Cpa | D-3Pal | Ser | Lys (Nic) | D-Lys(Nic) | Leu | Ilys | Pro | D-Ala-NH$_2$ |
| 23 | Azaline A | Ac-D-2Nal | D-4Cpa | D-3Pal | Ser | Lys (Atz) | D-Lys (Atz) | Leu | Ilys | Pro | D-Ala-NH$_2$ |
| 24 | Azaline B | Ac-D-2Nal | D-4Cpa | D-3Pal | Ser | Aph (Atz) | D-Aph (Atz) | Leu | Ilys | Pro | D-Ala-NH$_2$ |
| 25 | Cetrorelix | Ac-D-2Nal | D-4Cpa | D-3Pal | Ser | Tyr | D-Cit | Leu | Arg | Pro | D-Ala-NH$_2$ |
| 26 | Degarelix | Ac-D-2Nal | D-4Cpa | D-3Pal | Ser | Aph (L-Hor) | D-Aph (Cbm) | Leu | Ilys | Pro | D-Ala-NH$_2$ |
| 27 | Ganirelix | Ac-D-2Nal | D-4Cpa | D-3Pal | Ser | Tyr | hArg(Et)$_2$ | Leu | hArg(Et)$_2$ | Pro | D-Ala-NH$_2$ |
| 28 | nafarelin | 5-oxo-Pro | His | Trp | Ser | Tyr | D-2Nal | Leu | Arg | Pro | Gly-NH$_2$ |
| 29 | Nal-Glu | Ac-D-2Nal | D-4Cpa | D-3Pal | Ser | Arg | p-mb-D-2Abu | Leu | Arg | Pro | D-Ala-NH$_2$ |
| 30 | Nictide | Ac-D-2Nal | D-4Cpa | D-3Pal | Ser | PicLys | D-(6-amino-Nic)-Orn | Leu | Ilys | Pro | D-Ala-NH$_2$ |

TABLE 2-continued

| SEQ ID NO | | | | | | | | | | |
|---|---|---|---|---|---|---|---|---|---|---|
| 36 | GnRH-I | pGlu | His | Trp | Ser | Tyr | Gly | Leu | Arg | Pro | Gly-NH$_2$ |
| 31 | A-76154 | H | Phe | Trp | Ser | Tyr | D-Trp | Leu | Arg | Pro | NHEt |
| 32 | A-75998 | Ac-D-2Nal | D-4Cpa | D-3Pal | Ser | N-Me-Tyr | D-Lys (Nic) | Leu | Ilys | Pro | D-Ala-NH$_2$ |
| 33 | FE 200486 | Ac-D-2Nal | D-4Cpa | D-3Pal | Ser | Aph (Hor) | D-Aph (Cpa) | Leu | Ilys | Pro | D-Ala-NH$_2$ |
| 34 | ORG-30850 | Ac-D-4Cpa | D-4Cpa | D-3Pal | Ser | Tyr | D-Lys | Leu | Arg | Pro | D-Ala-NH$_2$ |
| 35 | Org 30276 | Ac-D-4Cpa | D-4Cpa | D-Trp | Ser | Tyr | D-Arg | Leu | Arg | Pro | D-Ala-NH$_2$ |
| 44 | | Ac-D-2Nal | D-4Cpa | D2-OMe-5Pal | Ser | Aph (L-Hor) | D-Aph (Cbm) | Leu | Ilys | Pro | D-Ala-NH$_2$ |
| 45 | | Ac-D-2Nal | D-4Cpa | L2-OMe-5Pal | Ser | Aph (L-Hor) | D-Aph (Cbm) | Leu | Ilys | Pro | D-Ala-NH$_2$ |

A-198401 Abbott 11-deoxy-11-[carboxy(3,4-dichlorophenethyl) amino]-3-O-[4-(S)-methyl-oxazolidin-2-one] carbamoyl-5-O-(3N-desmethyl-3N-cyclopropylmethyl) desosaminyl-6-O-methyl-erythronolide A 11,12-(cyclic carbamate Abbreviations:
Abu is 2-aminobutyric acid;
p-mb-D-2Abu is (p-methoxybenzoyl)-D-2Abu;
Ac is acetyl;
Aph is 4-aminophenylalanine;
Atz is [5'-(3'-amino-1H-1',2',4'-triazoyl)];
Cbm is carbamoyl;
hArg(Et)$_2$ is NG,NG-diethyl-homoarginine;
Hci is homocitrulline;
Hor is hydroorotyl;
Ilys is N$^\omega$-isopropyllysine;
Nic is nicotinyl;
Orn is ornitine;
PicLys is N-picolinoyllysine
2OMe-5 Pal is 3-(2-methoxy-5-pyridyl)-alanine Unless otherwise indicated, the amino acids mentioned in the tables above are in the naturally occurring L-form.

An important aspect of the GnRH II antagonists according to the present invention is the substitution of the amino acid at position 1 of the naturally occurring GnRH II (SEQ ID NO 18). With a specific substitution at position 1 the GnRH II peptide can be converted from an agonist into an antagonist.

Preferably, the amino acid at position 6 of the above sequence, X$_5$, is a D-amino acid in view of its stability and the conformation of the peptide. Particularly preferred is said amino acid D-Lys or D-3 Pal.

In addition, amino acid 10, X$_8$, is particularly preferred D-Ala.

Particularly preferred are the peptide according to Seq-ID.No 37 to 43 and derivatives thereof.

In a further embodiment, the present invention relates to compounds of the general formula below (Seq.-ID No. 46) having a GnRH II antagonistic activity:

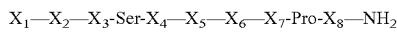

$$X_1-X_2-X_3-Ser-X_4-X_5-X_6-X_7-Pro-X_8-NH_2$$

wherein
X1=Ac-D-2Nal, Ac-$\Delta^3$Pro
X2=His, D-4 Cpa, Arg, Tyr, Trp, D-4Fpa, D-4 Bpa
X3=Trp, D-3 Pal, D-2Nal, Ala, Phe, His
X4=Tyr, His
X5=D-Lys, D-Trp, D-3 Pal, D-2Nal
X6=Trp, Leu, Arg
X7=Tyr, Leu, Arg
X8=D-Ala, D-Gly, D-Cys, D-Ser, D-Val, D-Thr, D-Pro, D-Ile, D-Leu or derivatives thereof.

Preferably, the compound of the general formula is a compound wherein X1 is Ac-D-2Nal, X2 is D-4-Cpa, D-4-Fpa or D-4 Bpa, X3 is D-3 Pal, X5 is D-Lys or D-3 Pal, X6 is Trp, X7 is Tyr or Leu and X8 is D-Ala. Particularly preferred, the compound is a compound selected from the group of Seq. ID. No. 37 to 43.

As indicated above, the peptide GnRH II antagonist includes derivatives like peptide mimetics of the subject peptides. A peptide mimetic is a non-naturally occurring analog of a peptide which, because of protective groups at one or both ends of the mimetic, or replacement of one or more peptide bonds with non-peptide bonds, is less susceptible to proteolytic cleavage than the peptide itself. For instance, one or more peptide bonds can be replaced with an alternative type of covalent bond (e.g., a carbon-carbon bond or an acyl bond). Peptide mimetics can also incorporate amino-terminal or carboxyl terminal blocking groups such as t-butyloxycarbonyl, acetyl, alkyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl, thereby rendering the mimetic less susceptible to proteolysis. Non-peptide bonds and carboxyl- or amino-terminal blocking groups can be used singly or in combination to render the mimetic less susceptible to proteolysis than the corresponding peptide. Additionally, substitution of D-amino acids for the normal L-stereoisomer can be effected, e.g. to increase the half-life of the molecule.

Accordingly, the peptide mimetics include peptides having one or more of the following modifications:

peptides wherein one or more of the peptidyl [—C(O)NR—] linkages (bonds) have been replaced by a non-peptidyl linkage such as a —CH$_2$-carbamate linkage [—CH$_2$—OC(O)NR—]; a phosphonate linkage; a —CH$_2$-sulfonamide [—CH$_2$—S(O)$_2$NR—] linkage; a urea [—NHC(O)NH—] linkage; a —CH$_2$-secondary amine linkage; or an alkylated peptidyl linkage [—C(O)NR$^6$]— where R$^6$ is lower alkyl;

peptides wherein the N-terminus is derivatized to a —NRR$^1$ group; to a —NRC(O)R group; to a —NRC(O)OR group; to a —NRS(O)$_2$R group; to a —NHC(O)NHR group, where R and R$^1$ are hydrogen or lower alkyl with the proviso that R and R$^1$ are not both hydrogen: to a succinimide group; to benzyloxycarbonyl-NH—(CBZ-NH—) group; or to a benzyloxycarbonyl-NE-group having from 1 to 3 substituents on the phenyl ring selected from the group consisting of lower alkyl, lower alkoxy, chloro, and bromo; or peptide wherein the C terminus is derivatized to —C(O)R$^2$ where R$^2$ is selected from the group consisting of C1-C6 alkoxy, and —NR$^3$R$^4$ where R$^3$ and R$^4$ are independently selected from the group consisting of hydrogen and C1-C6 alkyl.

Preferred mimetics have from zero to all of the —C(O) NH— linkages of the peptide replaced by a linkage selected from the group consisting of a —CR$_2$OC(O)NR— linkages; a phosphate linkage; a —CH$_2$S(O)$_2$NR— linkage; a —CH$_2$NR-linkage; and a —C(O)NR$^6$-linkage, and a —NHC(O)NH-linkage where R is hydrogen or lower alkyl and R$^6$ is lower alkyl, and wherein the N-terminus of the mimetic is selected from the group consisting of a —NRR$^1$ group; a —NRC(O)R group; a —NRC(O)OR group; a —NRS(O)$_2$R group; a —NHC(O)NHR group; a succinimide group; a benzyloxycarbonyl-NH-group; and a benzyloxycarbonyl-NH-group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of the mimetic has the formula —C(O)R$^2$ where R$^2$ is selected from the group consisting of hydroxyl, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide, and physiologically acceptable salts thereof.

Particularly preferred, the peptides are modified with an acetyl group at the N-terminus. In another embodiment, the peptides are particularly modified with a —NR$^3$R$^4$ group wherein each of R$^3$ and R$^4$ are hydrogen at the C-terminus.

The term "lower" as used herein, means a C1-C6 group, which may be in a linear, branched or cyclic form.

Of course, it is also possible to use non-peptide structures having a GnRH II activity. Thus, the present invention also allows for screening specific apoptosis inducing agents by selecting compounds for their GnRH II antagonistic activity. The skilled person is well aware of applying appropriate approaches for doing so.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet, for example under http://www.ncbi.nlm.nih.gov/PubMed/medline.html. Further databases and addresses, such as http://www.ncbi.nlm.nih.gov/, http://www.infobiogen.fr/, http://www.fmi.ch/biology/research_tools.html, http://www.tiqr.org/, are known to the person skilled in the art and can also be obtained using, e.g., http://www.google.de. An overview of patent information in biotechnology and a survey of relevant sources of patent information useful for retrospective searching and for current awareness is given in Berks, TIBTECH 12 (1994), 352-364.

The present invention is further described by reference to the following non-limiting figures and examples.

EXAMPLES

Apoptosis Assays

To quantify apoptosis we used a procedure similar to that described by Nicoletti et al. (J. Immunol. Methods 1991; 139:271-279) that was based on detecting advanced DNA degradation. Briefly, a pellet containing 1×10$^6$ cells was gently resuspended in 500 mL of hypotonic fluorochrome solution containing 0.1% Triton X-100 (Sigma, Deisenhofen, Germany), 0.1% sodium citrate, and 50 mg/mL propidium iodide (Sigma). The cell suspensions were placed at 4° C. in the dark overnight before flow cytometry analysis of cellular DNA content on a FACScalibur equipment (Becton Dickinson Immunocytometry Systems, Mountain View, Calif.) was performed with Cellquest software (Becton Dickinson Immunocytometry Systems). Cells were exposed to increasing concentrations of the GnRH-II antagonists from 10$^{-13}$ M to 10$^{-7}$ M for 72 hours before they were harvested.

The test was conducted using the MCF-7 breast cancer cell line, the endometrial cancer cell line Ishikawa and the prostate cancer cell line LNCAP. All cell lines are commercially available, e.g. via ATCC.

Anti Human GnRH-II Receptor Antiserum

Two rabbits were immunized with 2 mg of a peptide (YSPTMLTEVPPC) corresponding to the third extra cellular domain coupled to keyhole limpet haemocyanin via the Cys residue in complete Freund's adjuvant followed by three individual boosters in three week intervals in incomplete Freund's adjuvant. Blood was collected by heart punction (Peptide Specialty Laboratories, Heidelberg, Germany). Between the boosters and especially before the bleeding a small amount of blood was tested against ovalbumin conjugated peptide to determine the titer of the corresponding serum.

The antiserum was pre-absorbed using LTEVPP and PSMATEAPPC to avoid possible cross-reactions.

Immune Histology

Ovaries from marmoset monkey were fixed using 4% paraformaldehyde in PBS at 4° C. overnight, dehydrated, and embedded in paraffin. Then, sections of 4 μm thickness were prepared and put on silane coated slides. These slides were deparaffinized and rehydrated. Antigens were retrieved by incubation with 0.01 M citrate buffer (pH 6.0) in a microwave (700 W) for 5 minutes. Endogenous peroxidase activity was quenched by treatment with 3% hydrogen peroxide solution for 6 minutes. After washing in PBS, the slides were treated with polyclonal rabbit anti human GnRH-II receptors antiserum in an 1:10,000 dilution in 1% BSA in TBST [10 mm Tris (pH 8.0), 500 mm NaCl, and 0.1% Tween 20] for 1 h, and after being washed, were detected with the ready-to-use secondary antibody horseradish peroxidase-conjugated anti rabbit IgG detection system according to the instructions of the supplier (Zymed Laboratories, San Francisco, Calif.). Controls were performed by substitution of the primary antiserum with pre-immune serum of the same rabbit. Counterstaining was performed using Meyer's hematoxylin for 10 seconds. Then, the slides were dehydrated, cleared, mounted with Permount and studied by light microscopy.

Western Blot Analysis of the GnRH II Receptor Like Antigenicity in Various Human Cell Lines.

Western blot analysis of cell membrane preparations of human endometrial (FIG. 6 A, B) and ovarian (FIG. 6 C, D) cancer cell lines, which have been treated according to standard procedures, yielded a band at approximately 43 kDa whereas western blot analysis of cell membrane preparations of ovaries obtained from marmoset monkey yielded a band at approximately 54 kDa as shown on the same blot (FIG. 6 E). Western blot analysis of the human ovarian cancer cell line EFO-27 and of human placenta showed a much weaker band at 43 kDa (not shown). Using the same quantity of protein, the GnRH-II receptor-like protein seems to be much more expressed in the marmoset monkey. To detect a similar intensity of the bands within the western blot a 40-fold higher protein quantities of the human cancer cell lines were needed.

In vivo Evaluation of GnRH-II Antagonists.

Female athymic (nude) mice (CD1 nu/nu), 6 to 8 weeks old on arrival, were obtained from Charles River (Sulzfeld, Germany). The mice were housed in sterile cages in a temperature-controlled room with 12-hour light/12-hour dark schedule and were fed autoclaved chow and water ad libidum. All experiments were done according to the German ethical guidelines and the German laws for protection of animals.

Tumors were initiated by s.c. injection of 1×10$^7$ cancer cells. After 2 weeks all animals had developed solid tumors of about 80 mm$^3$ and the treatment was initiated. The in vivo experiments were done as follows: 25 nmol of GnRH-II antagonists per mouse were injected intraperitoneally. Treatment was repeated every day (ovarian cancer) or every 2 days (endometrial and breast cancer). Tumor volumes were measured every 2 days (ovarian cancer) or once a week (endometrial and breast cancer). The mice were killed after 21 days.

It was known that after GnRH-I receptor knock-out the antiproliferative effects of GnRH-I agonists were abrogated while the effects of GnRH-II agonist [D-Lys6]GnRH-II were still existing [Gründker C, et al. (2004), European Journal of Endocrinology 151:141-149]. These data suggest that in these cancer cells the antiproliferative effects of GnRH-II are not mediated through the GnRH-I receptor. Using a polyclonal antiserum to the putative human GnRH-II receptor generated to a peptide corresponding to the third extracellular domain of the marmoset monkey GnRH-II receptor it is demonstrated herein that a GnRH-II receptor-like antigenicity in histological sections and in cell membrane preparations of different human cancers is present. It was possible to identify a GnRH-II receptor-like antigen as a GnRH-II binding site having a size of approximately 43 kD [Eicke N, Günthert A R, Viereck V, Siebold D, Béhé M, Becker T, Emons G, Gründker C (2005) GnRH-II receptor-like antigenicity in human in human placenta and in cancers of human reproductive organs. European Journal of Endocrinology, 153, 602-612.

Herein it is demonstrated that treatment of specific types of GnRH-II receptor-positive human cancer cells with GnRH-II antagonists results in apoptotic cell death. Co-treatment with GnRH-II agonist [D-Lys6]GnRH-II results in a dramatic decrease of apoptotic cell death indicating that GnRH-II antagonists induces apoptotic cell death specifically via binding to the GnRH-II receptor.

Further, it is demonstrated that the peptide according to Seq. ID. No. 37 has a higher activity than the peptide known as Trptorelix-2 described in WO 03/093304, Seq. ID No. 9, see FIGS. 7 and 8, respectively. Thus, it seems that the amino acid D-Lys at position 6 of the decapeptide is of particular importance. Furthermore, data not shown herein suggest that a D-amino acid at position 10 is particularly favorable since decapeptides having a Gly at position 10 showed a lower activity when compared to the same peptides having a D-Ala at position 10.

The effectiveness the GnRH-II antagonists could be confirmed impressively in nude mice. The GnRH-II antagonists impeded the growth of xenotransplants of the above-mentioned tumor entities in nude mice high significant, without any visible side effects (FIGS. 9-11).

Thus, the present invention provides compounds useful in the treatment of various diseases in particular of cancer wherein said cancer cells and its precursor cells express the GnRH II receptor. In addition, the present invention concerns to new compounds having a higher activity in inducing apoptosis via the GnRH II receptor than compounds described in the art.

The invention claimed is:

1. An isolated peptide compound which is a GnRH II antagonist having the general formula (Seq. ID No. 46):

$X_1—X_2—X_3$-Ser-$X_4—X_5—X_6—X_7$-Pro-$X_8—NH_2$ wherein

X1=Ac-D-2Nal

X2=D-4Cpa, D-4Fpa, or D-4Bpa,

X3=D-3Pal

X4=Tyr, or His

X5=D-Lys, D-3Pal

X6=Trp

X7=Tyr, or Leu

X8=D-Ala.

2. The compound according to claim 1, wherein the compound is selected from the group consisting of:

Ac-D-2Nal-D-4Cpa-D-3Pal-Ser-His-D-Lys-Trp-Tyr-Pro-D-Ala-NH$_2$ (SEQ ID:NO 37);

Ac-D-2Nal-D-4Cpa-D-3Pal-Ser-His-D-Lys-Trp-Leu-Pro-D-Ala-NH$_2$ (SEQ ID:NO 38);

Ac-D-2Nal-D-4Cpa-D-3Pal-Ser-Tyr-D-Lys-Trp-Tyr-Pro-D-Ala-NH$_2$ (SEQ ID:NO 39);

Ac-D-2Nal-D-4Cpa-D-3Pal-Ser-Tyr-D-Lys-Trp-Leu-Pro-D-Ala-NH$_2$ (SEQ ID:NO 40);

Ac-D-2Nal-D-4Cpa-D-3Pal-Ser-His-D-3Pal-Trp-Leu-Pro-D-Ala-NH$_2$ (SEQ ID:NO 41);

Ac-D-2Nal-D-4Cpa-D-3Pal-Ser-Tyr-D-3Pal-Trp-Tyr-Pro-D-Ala-NH$_2$ (SEQ ID:NO 42) and Ac-D-2Nal-D-4Cpa-D-3Pal-Ser-Tyr-D-3Pal-Trp-Leu-Pro-D-Ala-NH$_2$ (SEQ ID:NO 43).

3. A pharmaceutical composition comprising the isolated peptide a compound of claim 1 and a pharmaceutically acceptable carrier.

4. The pharmaceutical composition according to claim 3, wherein the compound is selected from the group consisting of:

Ac-D-2Nal-D-4Cpa-D-3Pal-Ser-His-D-Lys-Trp-Tyr-Pro-D-Ala-NH$_2$ (SEQ ID:NO 37);

Ac-D-2Nal-D-4Cpa-D-3Pal-Ser-His-D-Lys-Trp-Leu-Pro-D-Ala-NH$_2$ (SEQ ID:NO 38);

Ac-D-2Nal-D-4Cpa-D-3Pal-Ser-Tyr-D-Lys-Trp-Tyr-Pro-D-Ala-NH$_2$ (SEQ ID:NO 39);

Ac-D-2Nal-D-4Cpa-D-3Pal-Ser-Tyr-D-Lys-Trp-Leur-Pro-D-Ala-NH$_2$ (SEQ ID:NO 40);

Ac-D-2Nal-D-4Cpa-D-3Pal-Ser-His-D-3Pal-Trp-Leu-Pro-D-Ala-NH$_2$ (SEQ ID:NO 41);

Ac-D-2Nal-D-4Cpa-D-3Pal-Ser-Tyr-D-3Pal-Trp-Tyr-Pro-D-Ala-NH$_2$ (SEQ ID:NO 42) and Ac-D-2Nal-D-4Cpa-D-3Pal-Ser-Tyr-D-3Pal-Trp-Leu-Pro-D-Ala-NH$_2$ (SEQ ID:NO 43).

* * * * *